(12) United States Patent
Zhang

(10) Patent No.: US 12,217,838 B2
(45) Date of Patent: Feb. 4, 2025

(54) PHYSICAL EXAMINATION INFORMATION DISTRIBUTION TO DISTRIBUTION OBJECTS WITH WORKLOAD INFORMATION AND MATCHING MODEL

(71) Applicant: BOE TECHNOLOGY GROUP CO., LTD., Beijing (CN)

(72) Inventor: Zhenzhong Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 683 days.

(21) Appl. No.: 17/440,219

(22) PCT Filed: Dec. 25, 2020

(86) PCT No.: PCT/CN2020/139523
§ 371 (c)(1),
(2) Date: Sep. 17, 2021

(87) PCT Pub. No.: WO2022/134032
PCT Pub. Date: Jun. 30, 2022

(65) Prior Publication Data
US 2022/0406418 A1      Dec. 22, 2022

(51) Int. Cl.
*G06F 40/279*      (2020.01)
*G06F 40/205*      (2020.01)
(Continued)

(52) U.S. Cl.
CPC .......... *G16H 10/60* (2018.01); *G06F 40/205* (2020.01); *G16H 40/20* (2018.01)

(58) Field of Classification Search
CPC ... G06F 40/279; G06F 40/284; G06N 3/0455; G06N 20/00; G06N 3/048; G16H 10/00; G16H 10/60; G16H 40/00; G16H 40/20
(Continued)

(56) References Cited

U.S. PATENT DOCUMENTS 9,424,532 B1 *   8/2016   Abedini ................. G06N 20/00
10,061,894 B2 *  8/2018   Sethumadhavan .... G16H 40/20
(Continued)

FOREIGN PATENT DOCUMENTS

CN      102332052 A      1/2012
CN      103356166 A     10/2013
(Continued)

*Primary Examiner* — Martin Lerner
(74) *Attorney, Agent, or Firm* — WHDA, LLP

(57) ABSTRACT

There are provided a method and an apparatus for distributing physical examination information, an electronic device, a computer-readable storage medium, and a computer program product. The method includes: obtaining physical examination information and information of a plurality of distribution objects; inputting the physical examination information and the information of the plurality of distribution objects into an information matching model obtained by pre-training to obtain a matching degree between the physical examination information and the plurality of distribution objects; and determining a target distribution object from the plurality of distribution objects according to the matching degree between the physical examination information and each of the plurality of distribution objects, and distributing the physical examination information to the target distribution object.

16 Claims, 8 Drawing Sheets

US 12,217,838 B2
Page 2

(51) Int. Cl.
*G06N 3/048* (2023.01)
*G16H 10/60* (2018.01)
*G16H 40/20* (2018.01)

(58) Field of Classification Search
USPC ............ 704/1, 9; 706/12; 705/2, 7.13, 7.14, 705/7.22
See application file for complete search history.

(56) References Cited

U.S. PATENT DOCUMENTS

| | | | | |
|---|---|---|---|---|
| 11,144,340 B2* | 10/2021 | Warnicke | ............... | G06F 9/5077 |
| 11,281,863 B2* | 3/2022 | Keskar | ................. | G06F 40/284 |
| 11,455,466 B2* | 9/2022 | Zhang | ................... | G06F 40/274 |
| 11,468,246 B2* | 10/2022 | Olabiyi | ................... | G06F 40/30 |
| 11,568,982 B1* | 1/2023 | Guttag | ................. | G16H 40/20 |
| 11,573,957 B2* | 2/2023 | Zeng | ..................... | G06F 40/284 |
| 11,675,631 B2* | 6/2023 | Martins | ............ | G06Q 10/06315 |
| | | | | 718/104 |
| 11,687,829 B2* | 6/2023 | Hanley | .................. | G06N 20/00 |
| | | | | 706/12 |
| 2009/0198733 A1* | 8/2009 | Gounares | ............... | G16H 40/20 |
| 2009/0259488 A1* | 10/2009 | Gounares | ............... | G16H 50/20 |
| | | | | 705/7.42 |
| 2012/0185416 A1* | 7/2012 | Baras | ...................... | G16H 40/20 |
| | | | | 706/12 |
| 2012/0185867 A1* | 7/2012 | Archer | ................... | G06F 9/5066 |
| | | | | 718/105 |
| 2015/0106117 A1 | 4/2015 | Ananda et al. | | |
| 2017/0076044 A1 | 3/2017 | Kogure | | |
| 2018/0326583 A1* | 11/2018 | Baroudi | ................. | B25J 9/1661 |
| 2018/0357472 A1 | 12/2018 | Dreessen | | |
| 2019/0043606 A1* | 2/2019 | Roots | ..................... | G16H 10/60 |
| 2019/0180868 A1* | 6/2019 | Makram | ................ | G06N 20/00 |
| 2019/0228524 A1 | 7/2019 | Chen et al. | | |
| 2019/0324799 A1* | 10/2019 | Metsch | .................. | G06N 20/00 |
| 2020/0241921 A1* | 7/2020 | Calmon | ................. | G06N 3/045 |
| 2021/0208943 A1* | 7/2021 | Baughman | ............. | G06N 20/00 |
| 2022/0147826 A1* | 5/2022 | Xiao | ...................... | G06N 3/045 |
| 2022/0180178 A1* | 6/2022 | Tasinga | .................. | G06N 3/063 |

FOREIGN PATENT DOCUMENTS

| | | | |
|---|---|---|---|
| CN | 106485056 A | 3/2017 | |
| CN | 107301616 A | 10/2017 | |
| CN | 108305671 A | 7/2018 | |
| CN | 109102867 A | 12/2018 | |
| CN | 109215779 A | 1/2019 | |
| CN | 109887567 A | 6/2019 | |
| CN | 110232971 A | 9/2019 | |
| CN | 110377714 A | 10/2019 | |
| CN | 110580942 A | 12/2019 | |
| CN | 110797101 A | 2/2020 | |
| CN | 110993081 A | 4/2020 | |
| CN | 111475713 A | 7/2020 | |
| WO | WO-2015173675 A1 * | 11/2015 | ....... G06F 16/24578 |

\* cited by examiner

Obtain physical examination information and information of a plurality of distribution objects, the physical examination information comprising abnormal physical examination information and workload information of the physical examination information, and the information of the plurality of distribution objects comprising specialty information and workload information of the plurality of distribution objects — S11

Input the physical examination information and the information of the plurality of distribution objects into an information matching model obtained by pre-training to obtain a matching degree between the physical examination information and the plurality of distribution objects, wherein the information matching model is configured to calculate the matching degree between the physical examination information and the plurality of distribution objects according to the abnormal physical examination information, the workload information of the physical examination information, and the specialty information and the workload information of the plurality of distribution objects — S12

Determine a target distribution object from the plurality of distribution objects according to the matching degree between the physical examination information and each of the plurality of distribution objects, and distribute the physical examination information to the target distribution object — S13

FIG. 1

Obtain a plurality of training sample pairs, each of the plurality of training sample pairs being a first sample pair or a second sample pair, the first sample pair comprising sample physical examination information and information of a first sample distribution object, the second sample pair comprising the sample physical examination information and information of a second sample distribution object, wherein the matching degree of the first sample pair is greater than that of the second sample pair, the sample physical examination information comprises abnormal sample physical examination information, information of a sample distribution object comprises specialty information of the sample distribution object, and the sample distribution object is the first sample distribution object or the second sample distribution object — S51

Input the training sample pair into a model to be trained to obtain the matching degree of the training sample pair — S52

Train the model to be trained according to the matching degree of the first sample pair, the matching degree of the second sample pair, workload information of the sample physical examination information, and workload information of each of the sample distribution objects, to determine the model to be trained after training as the information matching model — S53

FIG. 5

PHYSICAL EXAMINATION INFORMATION DISTRIBUTION TO DISTRIBUTION OBJECTS WITH WORKLOAD INFORMATION AND MATCHING MODEL

TECHNICAL FIELD

The present disclosure relates to the field of computer technologies, and more particularly, to a method and an apparatus for distributing physical examination information, an electronic device, a computer-readable storage medium, and a computer program product.

BACKGROUND

After a user completes a series of physical examination items (such as internal medicine examination, surgical examination, electrocardiogram, etc.), physical examination information may also include a general examination conclusions and health advices in addition to examination results (for example, electrocardiogram: normal sinus rhythm) for each of the physical examination items. The general examination conclusions and the health advices are health assessments and advices made by a general examining physician in accordance with the examination results in the physical examination information. In practical application, accuracy of the health assessments and advices cannot be ensured unless the physical examination information is distributed to appropriate general examining physicians.

Therefore, how to match the physical examination information with the general examining physician is a technical problem to be solved by those skilled in the art.

SUMMARY

The present disclosure provides a method and an apparatus for distributing physical examination information, an electronic device, a computer-readable storage medium, and a computer program product. Technical solutions of the present disclosure are as below.

According to a first aspect of the present disclosure, a method for distributing physical examination information is provided, the method comprising:

obtaining physical examination information and information of a plurality of distribution objects, the physical examination information comprising abnormal physical examination information and workload information of the physical examination information, and the information of the plurality of distribution objects comprising specialty information and workload information of the plurality of distribution objects;

inputting the physical examination information and the information of the plurality of distribution objects into an information matching model obtained by pre-training to obtain a matching degree between the physical examination information and the plurality of distribution objects, wherein the information matching model is configured to calculate the matching degree between the physical examination information and the plurality of distribution objects according to the abnormal physical examination information, the workload information of the physical examination information, and the specialty information and the workload information of the plurality of distribution objects; and determining a target distribution object from the plurality of distribution objects according to the matching degree between the physical examination information and each of the plurality of distribution objects, and distributing the physical examination information to the target distribution object.

In an alternative implementation, the information matching model comprises a semantic vector model and a vector matching model, and the step of inputting the physical examination information and the information of the plurality of distribution objects into an information matching model obtained by pre-training to obtain a matching degree between the physical examination information and the plurality of distribution objects comprises:

inputting the physical examination information and the information of the plurality of distribution objects into the semantic vector model to output a first vector; and inputting the first vector into the vector matching model to output the matching degree between the physical examination information and the plurality of distribution objects.

In an alternative implementation, the step of inputting the physical examination information and the information of the plurality of distribution objects into the semantic vector model to output a first vector comprises:

splicing the physical examination information and the information of the plurality of distribution objects to obtain spliced information, wherein a header of the spliced information employs a marker symbol [CLS], and a separator [SEP] is employed between the physical examination information and the information of the plurality of distribution objects; and inputting the spliced information into the semantic vector model to output the first vector.

In an alternative implementation, the step of inputting the first vector into the vector matching model to output the matching degree between the physical examination information and the plurality of distribution objects includes:

calculating, by the vector matching model, the matching degree between the physical examination information and the plurality of distribution objects based on a formula as below:

$score = W_2^T \sigma(W_1 V_{[cls]} + b_1)$, wherein the score represents the matching degree between the physical examination information and the plurality of distribution objects, the $V_{[cls]}$ represents the first vector, the $W_1$ represents a first mapping matrix of the vector matching model, and the $W_2^T$ represents a transposition of a second mapping matrix $W_2$ of the vector matching model, the $b_1$ represents a bias matrix of the vector matching model, and the $\sigma$ represents an activation function of the vector matching model.

In an alternative implementation, the semantic vector model includes a BERT model.

In an alternative implementation, the vector matching model includes a fully-connected layer network model.

In an alternative implementation, before the step of inputting the physical examination information and the information of the plurality of distribution objects into an information matching model obtained by pre-training to obtain a matching degree between the physical examination information and the plurality of distribution objects, the method further comprises:

obtaining a plurality of training sample pairs, each of the plurality of training sample pairs being a first sample pair or a second sample pair, the first sample pair comprising sample physical examination information and information of a first sample distribution object, the second sample pair comprising the sample physical examination information and information of a second sample distribution object, wherein the matching degree of the first sample pair is greater than that of the second sample pair, the sample physical examination information comprises abnormal sample physical examination information, information of a sample distribution object comprises specialty information of the sample distribution object, and the sample distribution object is the first sample distribution object or the second sample distribution object;

inputting the training sample pair into a model to be trained to obtain the matching degree of the training sample pair; and training the model to be trained according to the matching degree of the first sample pair, the matching degree of the second sample pair, workload information of the sample physical examination information, and workload information of each of the sample distribution objects, to determine the model to be trained after training as the information matching model.

In an alternative implementation, the step of training the model to be trained according to the matching degree of the first sample pair, the matching degree of the second sample pair, workload information of the sample physical examination information, and workload information of each of the sample distribution objects, to determine the model to be trained after training as the information matching model comprises:

training the model to be trained with a goal of ensuring a differential between the matching degree of the first sample pair and the matching degree of the second sample pair to be greater than a first preset threshold, and a first parameter of each of the sample distribution objects to be equal, wherein the first preset threshold is greater than zero, the first parameter is configured for characterizing the workload of each of the sample distribution objects, and the first parameter is determined by the workload information of the sample physical examination information.

In an alternative implementation, the step of training the model to be trained with a goal of ensuring a differential between the matching degree of the first sample pair and the matching degree of the second sample pair to be greater than a first preset threshold, and a first parameter of each of the sample distribution objects to be equal comprises:

calculating the differential between the matching degree of the first sample pair and the matching degree of the second sample pair, and determining a first loss portion according to the differential and the first preset threshold;

determining a second loss portion according to a second parameter of the sample physical examination information, a third parameter of the plurality of sample distribution objects, and the first parameter of each of the sample distribution objects, wherein the second parameter is configured for characterizing the workload of the sample physical examination information, and the third parameter is configured for characterizing number of the plurality of sample distribution objects;

performing a weighted summation of the first loss portion and the second loss portion to obtain a loss function; and training the model to be trained with a goal of minimizing the loss function.

In an alternative implementation, the first loss portion is determined based on a formula as below:

$L1 = \Sigma_{(u_j, d_{ij})} \Sigma_{(u_j, d_{il})} [score(u_j, d_{il}) + \gamma - score(u_j, d_{ij})]_+$,
wherein the L1 represents the first loss portion, the $u_j$ represents the sample physical examination information, the $d_{ij}$ represents the information of the first sample distribution object, the $d_{il}$ represents the information of the second sample distribution object, the $(u_j, d_{ij})$ represents the first sample pair, the $(u_j, d_{il})$ represents the second sample pair, the $score(u_j, d_{il})$ represents the matching degree of the second sample pair, the $score(u_j, d_{ij})$ represents the matching degree of the first sample pair, and the $\gamma$ represents the first preset threshold.

The second loss portion is determined based on a formula as below:

$L2 = \Sigma_{i=1}^{M}(N/M - h_i)^2$, wherein the L2 represents the second loss portion, the N represents the second parameter, the M represents the third parameter, and the $h_i$ represents the first parameter of the sample distribution object i.

The loss function is determined based on a formula as below:

$L = L1 + \beta L2$, wherein the L represents the loss function, and the $\beta$ represents a harmonic parameter.

In an alternative implementation, when the information matching model comprises a semantic vector model and a vector matching model, the model to be trained comprises a first model to be trained and a second model to be trained, and the step of inputting the training sample pair into the model to be trained to obtain the matching degree of the training sample pair comprises:

inputting the training sample pair into the first model to be trained to obtain a vector of the training sample pair; and inputting the vector of the training sample pair into the second model to be trained to obtain the matching degree of the training sample pair.

The step of training the model to be trained according to the matching degree of the first sample pair, the matching degree of the second sample pair, workload information of the sample physical examination information, and workload information of each of the sample distribution objects, to determine the model to be trained after training as the information matching model comprises:

training the first model to be trained and the second model to be trained according to the matching degree of the first sample pair, the matching degree of the second sample pair, the workload information of the sample physical examination information, and the workload information of each of the sample distribution objects, to determine the first model to be trained after training as the semantic vector model and determine the second model to be trained after training as the vector matching model.

In an alternative implementation, the matching degree between the physical examination information and the target distribution object is greater than or equal to a second preset threshold value; or the matching degree between the physical examination information and the target distribution object is greater than the matching degree between the physical examination information and other distribution object, wherein the other distribution object is a distribution object other than the target distribution object in the plurality of distribution objects.

According to a second aspect of the present disclosure, an apparatus for distributing physical examination information is provided, and the apparatus includes:

an information obtaining module, configured to obtain physical examination information and information of a plurality of distribution objects, the physical examination information comprising abnormal physical examination information and workload information of the physical examination information, and the information of the plurality of distribution objects comprising specialty information and workload information of the plurality of distribution objects;

an information processing module, configured to input the physical examination information and the information of the plurality of distribution objects into an information matching model obtained by pre-training to obtain a matching degree between the physical examination information and the plurality of distribution objects, wherein the information matching model is configured to calculate the matching degree between the physical examination information and the plurality of distribution objects according to the abnormal physical examination information, the workload information of the physical examination information, and the specialty information and the workload information of the plurality of distribution objects; and an information distribution module, configured to determine a target distribution object from the plurality of distribution objects according to the matching degree between the physical examination information and each of the plurality of distribution objects, and distribute the physical examination information to the target distribution object.

According to a third aspect of the present disclosure, there is provided an electronic device, including:

a processor, and a memory configured to store instructions executable by the processor.

The processor is configured to execute the instructions to implement the method for distributing physical examination information according to the first aspect.

According to a fourth aspect of the present disclosure, there is provided a storage medium. Instructions in the storage medium are executable by a processor of an electronic device, whereby the electronic device is caused to perform the method for distributing physical examination information according to the first aspect.

According to a fifth aspect of the present disclosure, there is provided a computer program product. Instructions in the computer program product are executable by a processor of an electronic device, whereby the electronic device is caused to perform the method for distributing physical examination information according to the first aspect.

Described above is merely an overview of the technical solutions of the present disclosure. In order to more apparently understand the technical means of the present disclosure to implement in accordance with the contents of specification, and to more readily understand above and other objectives, features and advantages of the present disclosure, specific embodiments of the present disclosure are provided hereinafter.

BRIEF DESCRIPTION OF THE DRAWINGS

To describe the technical solutions in the embodiments of the present disclosure or the existing technologies more clearly, the accompanying drawings required for describing the embodiments or the existing technologies will be briefly introduced below. Apparently, the accompanying drawings in the following description are merely some embodiments of the present disclosure. To those of ordinary skills in the art, other accompanying drawings may also be derived from these accompanying drawings without creative efforts.

FIG. 1 illustrates a flowchart of a method for distributing physical examination information according to an exemplary embodiment;

FIG. 5 illustrates a flowchart of a model obtaining mode according to an exemplary embodiment;

DETAILED DESCRIPTION

Figure 2:
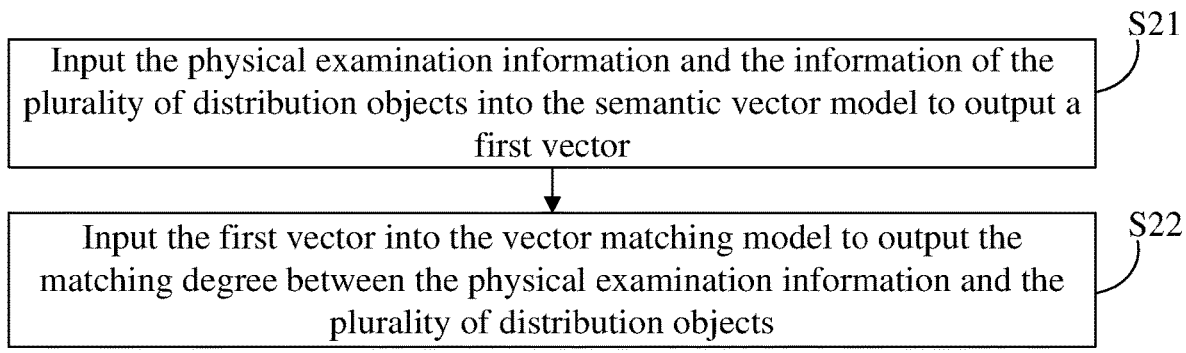
FIG. 2 illustrates a flowchart of matching degree calculation according to an exemplary embodiment.

To make the objectives, technical solutions, and advantages of the embodiments of the present disclosure clearer, the technical solutions in the embodiments of the present disclosure will be described clearly and completely below, in conjunction with the accompanying drawings in the embodiments of the present disclosure. Apparently, the described embodiments are some but not all of the embodiments of the present disclosure. All other embodiments obtained by a person of ordinary skill in the art based on the embodiments of the present disclosure without creative efforts shall fall within the protection scope of the present disclosure.

Assuming that a physical examination center has N pieces of physical examination information and M general examining physicians, one piece of physical examination information is distributed to each one of the M general examining physicians in turn. After the general examining physicians complete health assessments and advices, a system will sequentially distribute one piece of physical examination information from the remaining physical examination information to the general examining physicians in turn. Supposing there are two general examining physicians A and B in total, the physician A is good at internal medicine, and the physician B is good at surgery. In a physical examination information u, an internal medicine examination result is abnormal, and a surgical examination result is normal. Intuitively, the physical examination information u should be distributed to the general examining physician A. If the physical examination information u is distributed to the general examining physician B, this will lead to a problem of mismatching between the physical examination information and the general examining physician.

In addition, after the general examining physicians complete the health assessments and advices, the remaining physical examination information is to be distributed to the general examining physicians in turn. In this case, those efficient general examining physicians will have a heavy workload in the case of a certain total number of physical examination reports. For example, supposing that efficiency of the general examining physician A is twice that of the general examining physician B, the general examining physician A will complete 2N/3 reports, and the general examining physician B will complete N/3 reports. That is, the workload of the general examining physician A is twice that of the general examining physician B.

To accurately match the physical examination and distribution objects, FIG. 1 illustrates a flowchart of a method for distributing physical examination information according to an exemplary embodiment. As shown in FIG. 1, this method may include following steps.

Step S11: obtaining physical examination information and information of a plurality of distribution objects, the physical examination information comprising abnormal physical examination information and workload information of the physical examination information, and the information of the plurality of distribution objects comprising specialty information and workload information of the plurality of distribution objects.

An execution subject in this embodiment may be an electronic device such as a server, or may be a user terminal device such as a mobile phone or a computer.

The physical examination information may be, for example, a physical examination report in which a single examination result has been completed but it needs to provide a general examination result. The physical examination information may include examination results (for example, electrocardiogram examination results include sinus rhythm, etc.) of a series of physical examination items (such as general examination, internal medicine examination, electrocardiogram, and head CT, etc.).

In this embodiment, the physical examination information may include abnormal physical examination information, and the abnormal physical examination information may include abnormal examination results or abnormal physical examination items, etc. Specific contents of the abnormal physical examination information are not limited in this embodiment. The physical examination information may also include workload information of the physical examination information. The workload information of the physical examination information may be determined by, for example, a number of words in the abnormal examination results, etc. However, this embodiment is not limited thereto.

The distribution object may be, for example, a general examining physician. The information of the plurality of distribution objects may include specialty information of the plurality of distribution objects. The specialty information may include descriptions and introductions of the general examining physician's graduate institution, specialized subject, years of working, and adept examination items, etc. However, this embodiment does not limit the specific contents of the specialty information. For example, the specialty information may be as below: Dr. A, graduated from XX, . . . , worked for XX years, . . . , specializing in internal medicine. . . . The information of the plurality of distribution objects may also include workload information of the plurality of distribution objects, wherein the workload information may be determined by the number of physical examination reports that have been processed by the general examining physicians, e.g., Dr. A has processed M physical examination reports, and Dr. B has processed N physical examination reports, etc.

The physical examination information may be, for example, obtained from each single examination device, e.g., the examination results of each single examination device are provided by each sub-examining physician or are automatically provided by the device based on analysis. For example, the information of the plurality of distribution objects may be pre-entered and stored, e.g., entered by each physician through a user interaction interface.

Step S12: inputting the physical examination information and the information of the plurality of distribution objects into an information matching model obtained by pre-training to obtain a matching degree between the physical examination information and the plurality of distribution objects, wherein the information matching model is configured to calculate the matching degree between the physical examination information and the plurality of distribution objects according to the abnormal physical examination information, the workload information of the physical examination information, and the specialty information and the workload information of the plurality of distribution objects.

Specifically, the information matching model may calculate a specialty matching degree between the physical examination information and the plurality of distribution objects based on the abnormal physical examination information of the physical examination information and the specialty information of the plurality of distribution objects, and also may calculate a workload matching degree between the physical examination information and the plurality of distribution objects based on the workload information of the physical examination information and the workload information of the plurality of distribution objects. That is, the matching degree between the physical examination information and the plurality of distribution objects obtained by calculating in Step S12 includes the specialty matching degree and the workload matching degree between the physical examination information and the plurality of distribution objects.

When the physical examination information is a physical examination report and the distribution object is the general examining physician, the specialty matching between the physical examination information and the distribution object refers to a fact whether the examination results in the physical examination information are interpreted and processed by the general examining physician who is specialized in that examination results. For example, if there is an abnormal internal medicine examination result in the physical examination information u, an internist A is more professional to handle this physical examination report than a surgeon B. that is, the general examining physician A has a higher specialty matching with the physical examination report u.

The workload matching between the physical examination information and the plurality of distribution objects refers to a fact that the workload of the plurality of distribution objects can be equalized based on distribution of physical examination information.

In this embodiment, the information matching model may be obtained in advance by means of iterative training based on the sample physical examination information, the first sample distribution object, and the second sample distribution object, wherein the specialty matching degree between the first sample distribution object and the sample physical examination information is greater than the specialty matching degree between the second sample distribution object and the sample physical examination information. Specifically, during the training process, a first matching degree between the first sample distribution object and the sample physical examination information and a second matching degree between the second sample distribution object and the sample physical examination information may be calculated, and the information matching model is obtained by training with a goal of ensuring a differential between the first matching degree and the second matching degree to be greater than a first preset threshold, and the workload of the first sample distribution object and the workload of the second sample distribution object to be equalized. The specific training process of the information matching model will be described in detail in the subsequent embodiments.

By using the information matching model, a comprehensive consideration can be given to the matching degree between the plurality of distribution objects and the physical examination information in terms of specialty matching and workload matching, to ensure that the physical examination information can be distributed to the distribution object having a higher specialty matching, while ensuring a workload balance for each of the plurality of distribution objects.

Step S13: determining a target distribution object from the plurality of distribution objects according to the matching degree between the physical examination information and each of the plurality of distribution objects, and distributing the physical examination information to the target distribution object.

In specific implementation, the matching degree between the physical examination information and each of the plurality of distribution objects calculated in Step S12 may be used. Assuming that there are M distribution objects, the matching degree score between each of the M distribution objects and the physical examination information u may be obtained, and then a target distribution object may be determined based on the matching degree between the physical examination information and each of the M distribution objects, and the physical examination information is distributed to the target distribution object.

In some embodiments of the present disclosure, the order of execution of the steps is not limited, which may be adjusted according to actual needs.

In this embodiment, there are various implementations to determine the target distribution object from the plurality of distribution objects.

In one implementation, the matching degree between the physical examination information and the target distribution object may be greater than or equal to a second preset threshold. A specific value of the second preset threshold may be determined according to actual needs, which is not limited in this embodiment.

In another implementation, the matching degree between the physical examination information and the target distribution object may be greater than the matching degree between the physical examination information and other distribution objects. The other distribution objects are distribution objects other than the target distribution object in the plurality of distribution objects. In this implementation, a distribution object with the largest matching degree is determined as the target distribution object.

The physical examination information is represented by u, a set of information of the plurality of distribution objects is represented by $\{d_1, d_2, \ldots, d_N\}$, a value of the function $f(u, d_i) \in R+$ (R+ represents a positive real number) may be configured for measuring the matching degree between the physical examination information u and the information $d_i$ of the plurality of distribution objects, and the larger the value of the function is, the higher the matching degree between the physical examination information u and the distribution object is. In practical application, the physical examination report u is distributed to the target distribution object, wherein the information of the target distribution object may be expressed as $d^* = \max_{d_i}(f(u, d_i))$. That is, the target distribution object may be a distribution object, among the plurality of distribution objects, which has the highest matching degree with the physical examination report. In this embodiment, the function $f(u, d_i)$ represents the information matching model obtained by a pre-training.

The method for distributing physical examination information provided in this embodiment includes: obtaining physical examination information and information of a plurality of distribution objects; inputting the physical examination information and the information of the plurality of distribution objects into an information matching model obtained by pre-training to obtain a matching degree between the physical examination information and the plurality of distribution objects; and then determining a target distribution object from the plurality of distribution objects according to the matching degree between the physical examination information and each of the plurality of distribution objects, and distributing the physical examination information to the target distribution object. In this embodiment, by calculating the matching degree between the physical examination information and the plurality of distribution objects by means of the information matching model, a comprehensive consideration can be given to the matching degree between the plurality of distribution objects and the physical examination information in terms of specialty matching and workload matching, to ensure that the physical examination information can be distributed to the distribution object having a higher specialty matching, while ensuring a workload balance for each of the plurality of distribution objects. In this way, the matching between the physical examination information and the plurality of distribution objects is implemented.

In an alternative implementation, the information matching model comprises a semantic vector model and a vector matching model. With reference to FIG. 2, Step S12 may specifically include:

Step S21: inputting the physical examination information and the information of the plurality of distribution objects into the semantic vector model to output a first vector; and Step S22: inputting the first vector into the vector matching model to output the matching degree between the physical examination information and the plurality of distribution objects.

The semantic vector model is configured to map the physical examination information and the information of the plurality of distribution objects into the same vector space. The vector matching model is configured to calculate, in the vector space, the matching degree between the physical examination information and the plurality of distribution objects.

The physical examination information and the information of the plurality of distribution objects are greatly different from each other in terms of word form, but are semantically related to each other. Therefore, the physical examination information and the information of the plurality of distribution objects may be mapped into a semantic vector space, wherein semantically related contents are located close to each other in the semantic vector space. Therefore, the matching degree between the physical examination information and the information of the plurality of distribution objects may be measured in the semantic vector space.

In this step, the physical examination information and the information of the plurality of distribution objects are mapped into the same vector space by means of the semantic vector model obtained by pre-training, and then the matching degree between the physical examination information and the plurality of distribution objects is further calculated in this vector space.

The semantic vector model may be a language model such as a BERT model, an RNN model or an LSTM model, etc. The BERT model is a bi-directional language model in a true sense, and each word may utilize contextual information of this word at the same time. Therefore, the semantic vector model may use the BERT model to obtain a more accurate semantic vector to further improve the matching accuracy.

In this embodiment, the semantic vector model is obtained by training by means of the BERT model. In an alternative implementation, the physical examination information and the information of the plurality of distribution objects may be first spliced to obtain spliced information, wherein a header of the spliced information employs a marker symbol [CLS], and a separator [SEP] is employed between the physical examination information and the information of the plurality of distribution objects. Next, the spliced information is inputted into the semantic vector model to output the first vector.

Figure 3:
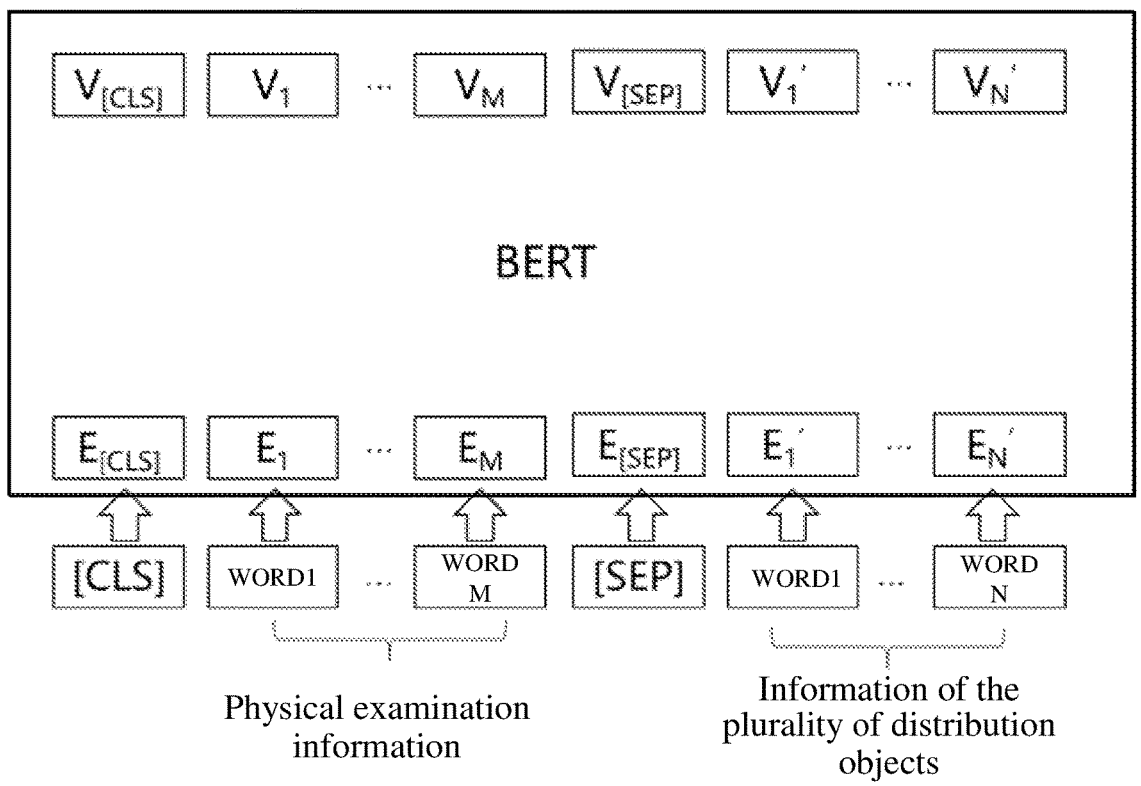
FIG. 3 illustrates a schematic diagram of processing information by a semantic vector model according to an exemplary embodiment.

In specific implementation, the physical examination information and the information of the plurality of distribution objects in text form may first be converted by using techniques such as word embedding to obtain a word vector. Referring to FIG. 3, "word i" represents the $i^{th}$ word in the corresponding text (the physical examination information or the information of the plurality of distribution objects), and the text "word i" corresponding to each word is transformed into a vector Ei or Ei' by means of word embedding, etc. Ei represents the word vector of the physical examination information, and Ei' represents the word vector of the information of the plurality of distribution objects. Next, Ei and Ei' may be used as initialization vectors, and the physical examination information and the information of the plurality of distribution objects in the form of word vector are spliced by means of the marker symbol [CLS] and the separator [SEP] to obtain the spliced information. Specifically, the marker symbol [CLS] may be added to the header of the spliced information, and the separator [SEP] may be added between the physical examination information u and the information d of the plurality of distribution objects. Next, the spliced information may be inputted as a whole into the semantic vector model such as the BERT model to obtain the first vector.

As the head of the spliced information, the marker symbol [CLS] represents that an output vector V[cls] corresponding to this symbol may be used as semantic representation or semantic vector of the spliced information. Semantic information of each word in the spliced information may be more "fairly" integrated by means of the marker symbol [CLS]. The separator [SEP] is configured for distinguishing the physical examination information in the spliced information from the information of the plurality of distribution objects.

As shown in FIG. 3, the first vector V[cls] is an output result of the semantic vector model, and the first vector V[cls] contains the physical examination information u and the information d of the plurality of distribution objects. In some embodiments, the first vector V[cls] represents a vector corresponding to the inputted physical examination information and the information of the plurality of distribution objects. When the semantic vector model employs the BERT model, dimensionality of the first vector V[cls] is 768 dimensions. In this implementation, a vector dimension of the BERT model is 768 dimensions by default. Of course, a vector in the BERT model may also have other dimensions, which is not limited in this embodiment. Vi or Vi' in FIG. 3 represents a vector outputted after the "word i" is processed by the semantic vector model.

In specific implementation, an information pair comprising the physical examination information and the information of each of the plurality of distribution objects may be inputted into the semantic vector model obtained by pre-training, to obtain the first vector corresponding to the inputted physical examination information and the information of the plurality of distribution objects. In this way, the physical examination information and the information of each of the plurality of distribution objects can be mapped into the same vector space by means of the semantic vector model.

In an alternative implementation, the vector matching model may employ a fully-connected layer network model. It is to be noted that the vector matching model is not limited to the fully-connected layer network model. Any network model that can transform an input vector into a scalar may be used as the vector matching model.

In an alternative implementation, the vector matching model may calculate the matching degree between the physical examination information and the plurality of distribution objects based on a formula as below:

score=$W_2^T \sigma(W_1 V_{[cls]}+b_1)$, wherein the score represents the matching degree between the physical examination information and the plurality of distribution objects, the $V_{[cls]}$ represents the first vector, the $W_1$ represents a first mapping matrix of the vector matching model, and the $W_2^T$ represents a transposition of a second mapping matrix $W_2$ of the vector matching model, the $b_1$ represents a bias matrix of the vector matching model, and the $\sigma$ represents an activation function of the vector matching model.

Figure 4:
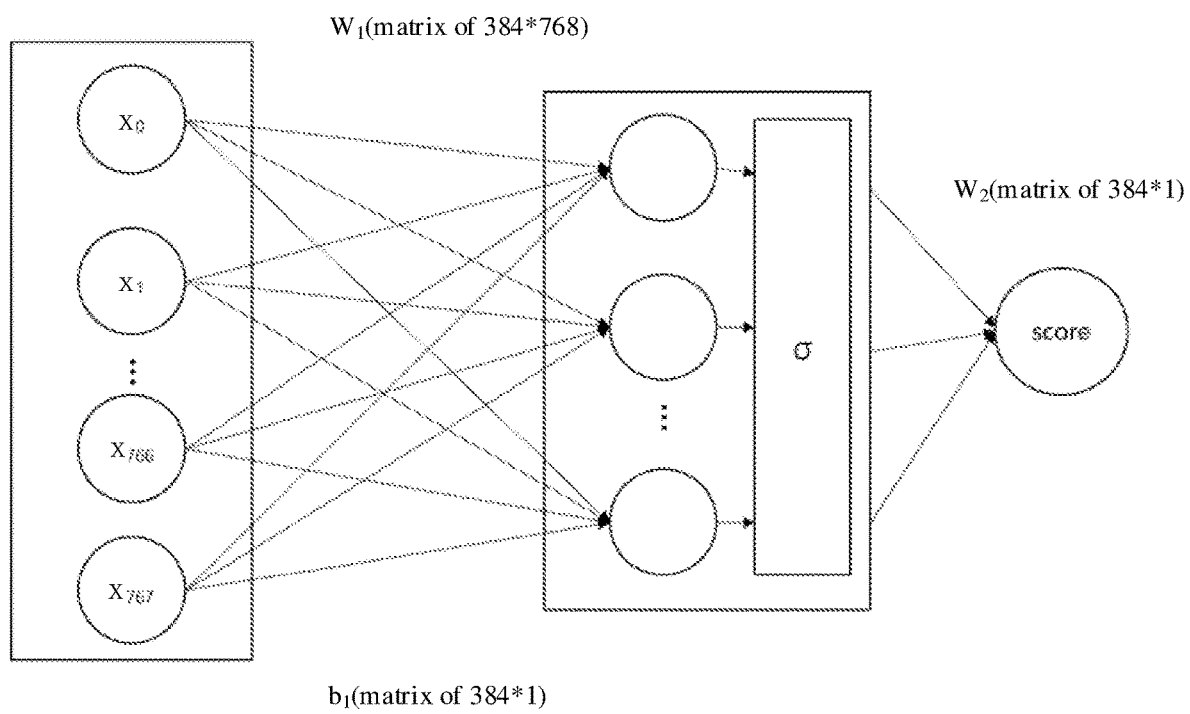
FIG. 4 illustrates a schematic diagram of processing information by a vector matching model according to an exemplary embodiment.

As shown in FIG. 4, the first vector V[cls] may be inputted into the vector matching model, to output the matching degree score between the physical examination information and the plurality of distribution objects. $x_i$ in FIG. 4 represents a value of the $i^{th}$ dimension in the first vector V[cls]. When the semantic vector model employs the BERT model, $W_1$ may represent a matrix of 384*768, and $W_2$ and $b_1$ may represent matrices of 384*1.

Parameters of the semantic vector model and parameters such as matrices W1, W2 and b1 in the vector matching model may be obtained by joint training. Parameters in a pre-trained model may be used as initial values of the parameters of the semantic vector model, and initial values of the matrices W1, W2 and b1 in the vector matching model may be obtained by means of random initialization. For example, the model is pre-trained using a mass of data to obtain the parameters in the pre-trained model, and then these parameters are finely adjusted on specific tasks. Specific training processes of the semantic vector model and the vector matching model will be described in detail in subsequent embodiments.

In this embodiment, the physical examination information and the information of the plurality of distribution objects are mapped into the same vector space by means of the semantic vector model, the matching degree between the physical examination information and each of the plurality of distribution objects is calculated in the vector space, and then the physical examination information is distributed to the appropriate distribution object according to the matching degree.

To obtain the information matching model, in an alternative implementation, referring to FIG. 5, before Step S12, the method for distributing physical examination information provided in this embodiment of the present disclosure may also include the following steps.

Step S51: obtaining a plurality of training sample pairs, each of the plurality of training sample pairs being a first sample pair or a second sample pair, the first sample pair comprising sample physical examination information and information of a first sample distribution object, the second sample pair comprising the sample physical examination information and information of a second sample distribution object, wherein the matching degree of the first sample pair is greater than that of the second sample pair, the sample physical examination information comprises abnormal sample physical examination information, information of a sample distribution object comprises specialty information of the sample distribution object, and the sample distribution object is the first sample distribution object or the second sample distribution object.

The sample physical examination information may be, for example, a sample physical examination report in which a single examination result has been completed but it needs to provide a general examination result. The sample physical examination information may include examination results (for example, electrocardiogram examination results include sinus rhythm, etc.) of a series of physical examination items (such as general examination, internal medicine examination, electrocardiogram, and head CT, etc.).

In this embodiment, the sample physical examination information may include abnormal sample physical examination information, and the abnormal sample physical examination information may include abnormal examination results or abnormal physical examination items, etc. Specific contents of the abnormal sample physical examination information are not limited in this embodiment.

The sample distribution object may be, for example, a general examining physician. The information of the plurality of sample distribution objects may include specialty information of the plurality of sample distribution objects. The specialty information may include descriptions and introductions of the general examining physician's graduate institution, specialized subject, years of working, and adept examination items, etc. However, this embodiment does not limit the specific contents of the specialty information. For example, the specialty information may be as below: Dr. A, graduated from XX, . . . , worked for XX years, . . . , specializing in internal medicine . . . .

In this embodiment, the first sample distribution object may be a sample distribution object having specialty matching with the sample physical examination information. That is, the specialty information of the first sample distribution object matches the abnormal sample physical examination information in the sample physical examination information. The second sample distribution object may be a sample distribution object having no specialty matching with the sample physical examination information. That is, the specialty information of the second sample distribution object does not match the abnormal sample physical examination information in the sample physical examination information. In the process of obtaining the training sample pair, the first sample distribution object and the second sample distribution object may be, for example, artificially specified based on the sample physical examination information and the information of the sample distribution object. For example, if the specialty matching degree of the first sample distribution object is greater than the specialty matching degree of the second sample distribution object, the first sample distribution object may be considered as a sample distribution object having specialty matching with the sample physical examination information, and the second sample distribution object may be considered as a sample distribution object having no specialty matching with the sample physical examination information.

The first sample pair $(u_j, d_{ij})$ includes the sample physical examination information $u_j$ and information $d_{ij}$ (wherein subscript ij $\in$ [1, M], and M represents a total number of sample distribution objects) of the first sample distribution object, and the second sample pair $(u_j, d_{il})$ includes the sample physical examination information $u_j$ and information $d_{il}$ (wherein subscript il $\in$ [1, M] and ij$\neq$il) of the second sample distribution object. The matching degree of the first sample pair $(u_j, d_{ij})$ may be greater than the matching degree of the second sample pair $(u_j, d_{il})$. That is, the sample physical examination information has a higher specialty matching with the first sample distribution object.

Step S52: inputting the training sample pair into a model to be trained to obtain the matching degree of the training sample pair.

Step S53: training the model to be trained according to the matching degree of the first sample pair, the matching degree of the second sample pair, workload information of the sample physical examination information, and workload information of each of the sample distribution objects, to determine the model to be trained after training as the information matching model.

The workload information of the sample physical examination information may be determined, for example, by a number of copies of the sample physical examination reports contained in the sample physical examination information, and also may be determined by number of words in the abnormal examination results, etc. However, this embodiment is not limited thereto.

The workload information of the sample distribution object may be determined by the workload of the sample physical examination information having specialty matching with the sample distribution object, for example, the number of the sample physical examination information having specialty matching with the sample distribution object.

In an alternative implementation, when the information matching model includes the semantic vector model and the vector matching model, the model to be trained includes a first model to be trained and a second model to be trained. Step S52 specifically may include: first inputting the training sample pair into the first model to be trained to obtain a vector of the training sample pair; and then inputting the vector of the training sample pair into the second model to be trained to obtain the matching degree of the training sample pair. Step S53 specifically may include: training the first model to be trained and the second model to be trained according to the matching degree of the first sample pair, the matching degree of the second sample pair, the workload information of the sample physical examination information, and the workload information of each of the sample distribution objects, to determine the first model to be trained after training as the semantic vector model and determine the second model to be trained after training as the vector matching model.

The first model to be trained may be a language model such as a BERT model, an RNN model, or an LSTM. The BERT model is a bi-directional language model in a true sense, and each word may utilize contextual information of this word at the same time. Therefore, the first model to be trained may use the BERT model to obtain a more accurate semantic vector to further improve the matching accuracy.

The second model to be trained may employ a fully-connected layer network model. It is to be noted that the second model to be trained is not limited to the fully-connected layer network model. Any network model that can transform an input vector into a scalar may be used as the second model to be trained.

In specific implementation, a training sample pair may be inputted into the first model to be trained to obtain a vector corresponding to the inputted training sample pair, and then the vector of the training sample pair is inputted into the second model to be trained to obtain the matching degree corresponding to the inputted training sample pair. In this way, the matching degrees of all the training sample pairs can be obtained, including the matching degree score $(u_j, d_{ij})$ of the first sample pair $(u_j, d_{ij})$ and the matching degree score $(u_j, d_{il})$ of the second sample pair $(u_j, d_{il})$. Next, the first model to be trained and the second model to be trained may be trained based on the matching degree of the first sample pair, the matching degree of the second sample pair, the workload information of the sample physical examination information, and the workload information of each of the sample distribution objects.

In an alternative implementation, in Step S53, the model to be trained may be trained with a goal of ensuring a differential between the matching degree score $(u_j, d_{ij})$ of the first sample pair and the matching degree score $(u_j, d_{il})$ of the second sample pair to be greater than a first preset threshold $\gamma$, and a first parameter of each of the sample distribution objects to be equal. The first preset threshold is greater than zero, and the sample distribution object is the first sample distribution object or the second sample distribution object. The first parameter is configured for characterizing the workload of each of the sample distribution objects, and the first parameter is determined by the workload information of the sample physical examination information. For example, the first parameter may be the workload of the sample physical examination information having specialty matching with the sample distribution object.

In some embodiments, "equal" may be exactly equal or the differential is less than a certain threshold, which may be set as needed.

Figure 6:
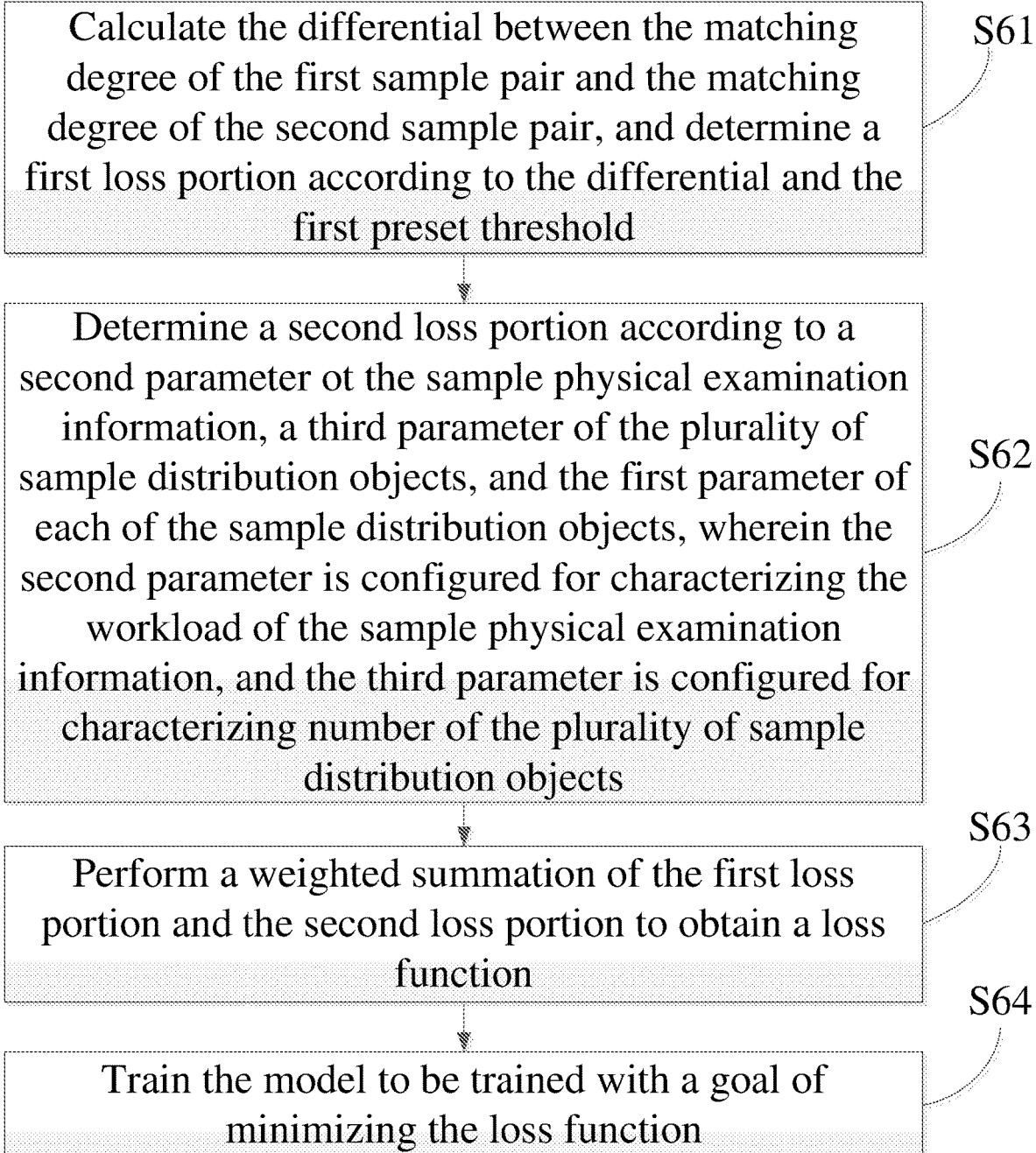
FIG. 6 illustrates a flowchart of a model training mode according to an exemplary embodiment.

Specifically, referring to FIG. 6, Step S53 may include following steps.

Step S61: calculating the differential between the matching degree of the first sample pair and the matching degree of the second sample pair, and determining a first loss portion according to the differential and the first preset threshold.

In practical application, a first training objective where the matching degree score$(u_j, d_{ij})$ of the first sample pair is at least higher by the first preset threshold $\gamma$ than the matching degree score$(u_j, d_{il})$ of the second sample pair may be determined, that is, score$(u_j, d_{ij})$>score$(u_j, d_{il})$+$\gamma$, wherein il $\in [1, M]$, ij $\in [1, M]$ and ij≠il. The first preset threshold is greater than zero. For example, the first preset threshold may be set to 1, but its specific value may be set according to the actual situations, and this embodiment is not limited thereto.

In specific implementation, the first loss portion may be determined based on a formula as below:

$L1 = \Sigma_{(u_j, d_{ij})} \Sigma_{(u_j, d_{il})} [\text{score}(u_j, d_{il}) + \gamma - \text{score}(u_j, d_{ij})]_+$, wherein the L1 represents the first loss portion, the $u_j$ represents the sample physical examination information, the $d_{ij}$ represents the information of the first sample distribution object, the $d_{il}$ represents the information of the second sample distribution object, the $(u_j, d_{ij})$ represents the first sample pair, the $(u_j, d_{il})$ represents the second sample pair, the score$(u_j, d_{il})$ represents the matching degree of the second sample pair, the score $(u_j, d_{ij})$ represents the matching degree of the first sample pair, and the $\gamma$ represents the first preset threshold. If $a \leq 0$, $[a]_+=0$; otherwise $[a]_+=a$.

Step S62: determining a second loss portion according to a second parameter of the sample physical examination information, a third parameter of the plurality of sample distribution objects, and the first parameter of each of the sample distribution objects, wherein the second parameter is configured for characterizing the workload of the sample physical examination information, and the third parameter is configured for characterizing a number of the plurality of sample distribution objects.

In this embodiment, it may be determined a second training objective where the first parameter of each of the sample distribution objects is equal, or it may be determined a second training objective where a differential between the first parameter of each of the sample distribution objects and an average workload is minimum, such that the model obtained by training can equalize the workload of each of the plurality of distribution objects.

In specific implementation, a ratio of the second parameter to the third parameter may be first calculated, and then the second loss portion is determined based on a differential between the first parameter and the ratio.

Assuming that the workload of each piece of sample physical examination information u is $u\_c_i$, where $i \in [1, k]$ and k represents the total number of pieces of sample physical examination information, the total workload (i.e., the second parameter) is $u\_c = \Sigma_1^k u_{c_i}$, the average workload is $$\overline{u\_c} = \frac{u\_c}{M},$$

and M represents the number of sample distribution objects, and serves as a third parameter. Assuming that the sample physical examination information matching the sample distribution object j includes $\{u_{j1}, \ldots, u_{jh}\}$, imbalance of workload of the sample distribution object may be represented by $V_j = (\overline{u\_c} - \Sigma_{l=1}^h u\_c_{jl})^2$, wherein $\Sigma_{l=1}^h u\_c_{jl}$ represents the workload (i.e., the first parameter) of the sample physical examination information having specialty matching with the sample distribution object j.

For a simplified description, in this embodiment it is assumed that the workload of each piece of physical examination information is the same, and is set to 1, i.e., $u_{c_i}=1$, i $\in [1, k]$. In this case, $$\overline{u\_c} = \frac{N}{M},$$

wherein N represents the total number of pieces of sample physical examination information, i.e., the second parameter, and M represents the number of sample distribution objects, i.e., the third parameter. Because $u_{c_i}=1$ and $i \in [1, k]$, the first parameter of the sample distribution object j is $\Sigma_{l=1}^{h_j} u\_c_{jl}=h_j$, and thus $$V_j = \left(\frac{N}{M} - h\right)^2.$$

In specific implementation, the second loss portion may be determined based on a formula as below:

$L2 = \Sigma_{i=1}^M (N/M - h_i)^2$, wherein the L2 represents the second loss portion, the N represents the second parameter, the M represents the third parameter, and the $h_i$ represents the first parameter of the sample distribution object i.

According to the calculation formula of the second loss portion, it can be known that when the number of pieces of sample physical examination information processed by each of the sample distribution objects is an average number N/M, the workload of each of the sample distribution objects is the same, i.e., the average workload. In this case, the loss of workload balance is the minimum, i.e., zero. However, the loss increases when the number of pieces of sample physical examination information processed by each of the sample distribution objects differs greatly.

Step S63: performing a weighted summation of the first loss portion and the second loss portion to obtain a loss function.

In specific implementation, the loss function may be determined based on a formula as below:

$L=L1+\beta L2$, wherein L represents the loss function, and $\beta$ represents a harmonic parameter.

Step S64: training the model to be trained with a goal of minimizing the loss function.

In specific implementation, the loss function may be minimized by using batch gradient descent to learn the model parameters.

In this embodiment, the loss of specialty matching degree between the sample physical examination information and each of the sample distribution objects is measured by means of the first loss portion, and the loss of workload balance of each sample distribution object is measured by means of the second loss portion. When the matching degree score$(u_j, d_{ij})$ of the first sample pair is at least higher by $\gamma$ than the matching degree score$(u_j, d_{ii})$ of the second sample pair and the workload (i.e., the first parameter) processed by each of the plurality of distribution objects is the same, the loss function L is minimized to zero.

As can be seen from the formula of the loss function L, if each piece of physical examination information is distributed to a distribution object having the highest specialty matching degree, this will cause a consequence that some distribution objects process a lot of physical examination information but some distribution objects process very little physical examination information. In this case, the first loss portion is smaller but the second loss portion is larger. In a model training process, the total loss function L may be minimized by adjusting the parameters, such that some physical examination information may be distributed to a distribution object having a higher specialty matching degree (such as the second or third highest specialty matching degree), to ensure the workload of the distribution objects to be balanced.

The information matching model may be obtained by training the model to be trained by using the above loss function. The semantic vector model and the vector matching model may be obtained by training the first model to be trained and the second model to be trained using the above loss function. The matching degree between new physical examination information and each of the plurality of distribution objects can be calculated by using the trained information matching model or the semantic vector model and the vector matching model, such that the target distribution object having a higher specialty matching degree and a balanced workload can be selected from the plurality of distribution objects.

By constructing the semantic vector model and the vector matching model, the physical examination information and the information of the plurality of distribution objects are mapped into the same vector space, and the target distribution object is determined in this vector space according to the specialty matching degree and the workload balance degree, and then the physical examination information is distributed to the target distribution object. In this solution, it is taken account of the specialty matching degree between the physical examination information and the plurality of distribution objects as well as the workload balance of each of the plurality of distribution objects. Compared with the traditional method, in this solution, the physical examination information can be distributed to a distribution target having a higher matching degree, while the workload of each of the plurality of distribution objects can be reasonably distributed, to achieve a workload balance for each of the plurality of distribution objects.

In practical application, the method for distributing physical examination information provided in this embodiment may be executed by a server, sent to a terminal, or executed by the terminal. This embodiment does not limit an execution subject of the method for distributing physical examination information.

Figure 7:
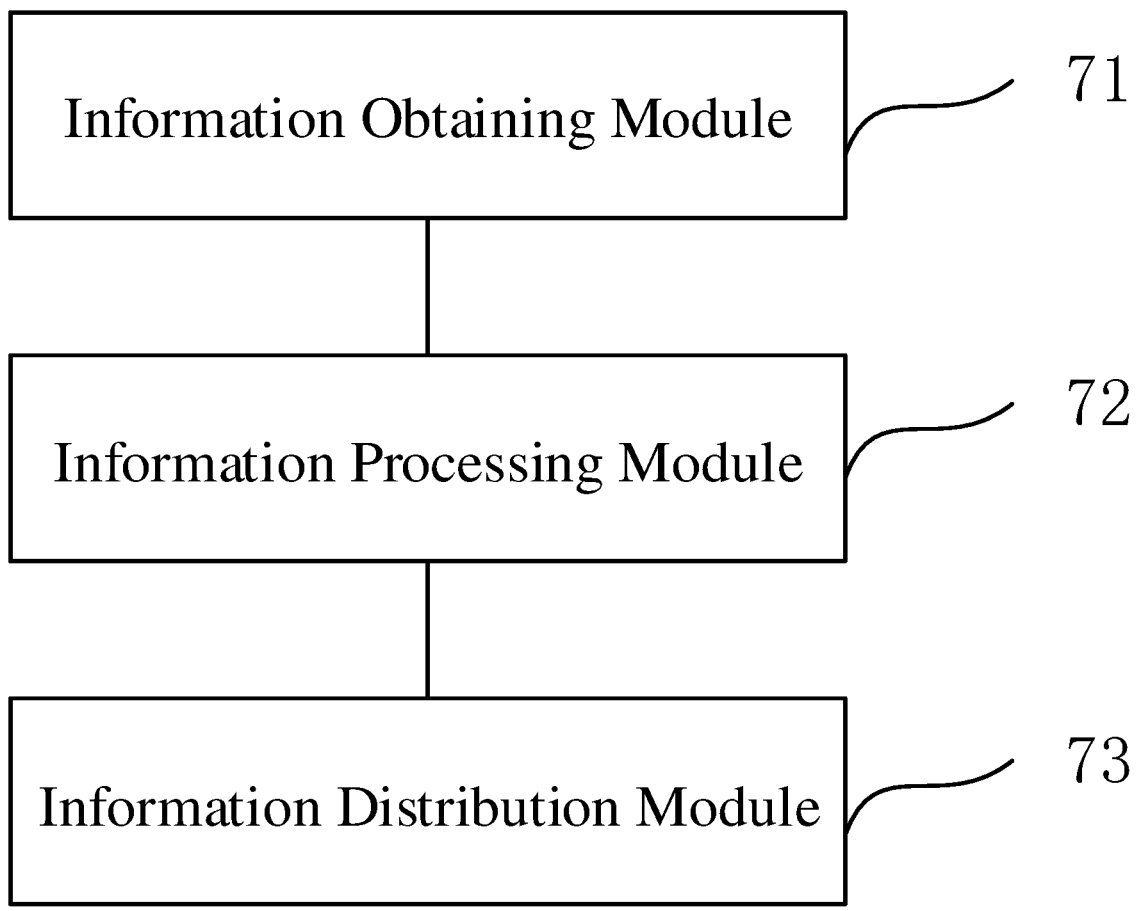
FIG. 7 illustrates a structural block diagram of an apparatus for distributing physical examination information according to an exemplary embodiment.

FIG. 7 illustrates a block diagram of an apparatus for distributing physical examination information according to an exemplary embodiment. Referring to FIG. 7, this apparatus may include:

an information obtaining module 71, configured to obtain physical examination information and information of a plurality of distribution objects, the physical examination information comprising abnormal physical examination information and workload information of the physical examination information, and the information of the plurality of distribution objects comprising specialty information and workload information of the plurality of distribution objects;

an information processing module 72, configured to input the physical examination information and the information of the plurality of distribution objects into an information matching model obtained by pre-training to obtain a matching degree between the physical examination information and the plurality of distribution objects, wherein the information matching model is configured to calculate the matching degree between the physical examination information and the plurality of distribution objects according to the abnormal physical examination information, the workload information of the physical examination information, and the specialty information and the workload information of the plurality of distribution objects; and an information distribution module 73, configured to determine a target distribution object from the plurality of distribution objects according to the matching degree between the physical examination information and each of the plurality of distribution objects, and distribute the physical examination information to the target distribution object.

The apparatus for distributing physical examination information provided in this embodiment may be applied to an electronic device such as a server, etc., or may also be applied to a user terminal device such as a mobile phone, or a computer, etc.

The physical examination information may be, for example, a physical examination report in which a single examination result has been completed but it needs to provide a general examination result. The physical examination information may include examination results (for example, electrocardiogram examination results include sinus rhythm, etc.) of a series of physical examination items (such as general examination, internal medicine examination, electrocardiogram, and head CT, etc.).

In this embodiment, the physical examination information may include abnormal physical examination information, and the abnormal physical examination information may include abnormal examination results or abnormal physical examination items, etc. Specific contents of the abnormal physical examination information are not limited in this embodiment. The physical examination information may also include workload information of the physical examination information. The workload information of the physical examination information may be determined, for example, by number of copies of the physical examination reports contained in the physical examination information, and also may be determined by a number of words in the abnormal examination results, etc. However, this embodiment is not limited thereto.

The distribution object may be, for example, a general examining physician. The information of the plurality of distribution objects may include specialty information of the plurality of distribution objects. The specialty information may include descriptions and introductions of the general examining physician's graduate institution, specialized subject, years of working, and adept examination items, etc. However, this embodiment does not limit the specific contents of the specialty information. For example, the specialty information may be as below: Dr. A, graduated from XX, . . . , worked for XX years, . . . , specializing in internal medicine . . . . The information of the plurality of distribution objects may also include workload information of the plurality of distribution objects, wherein the workload information may be determined by the number of physical examination reports that have been processed by the general examining physicians, e.g., Dr. A has processed M physical examination reports, and Dr. B has processed N physical examination reports, etc.

The physical examination information may be, for example, obtained by the information obtaining module 71 from each single examination device, e.g., the examination results of each single examination device are provided by each sub-examining physician or are automatically provided by the device based on analysis. For example, the information of the plurality of distribution objects may be pre-entered and stored, e.g., entered by each physician through a user interaction interface.

Specifically, the information matching model may calculate a specialty matching degree between the physical examination information and the plurality of distribution objects based on the abnormal physical examination information of the physical examination information and the specialty information of the plurality of distribution objects, and also may calculate a workload matching degree between the physical examination information and the plurality of distribution objects based on the workload information of the physical examination information and the workload information of the plurality of distribution objects. That is, the matching degree between the physical examination information and the plurality of distribution objects calculated by the information processing module 72 includes the specialty matching degree and the workload matching degree between the physical examination information and the plurality of distribution objects.

When the physical examination information is a physical examination report and the distribution object is the general examining physician, the specialty matching between the physical examination information and the distribution object refers to a fact whether the examination results in the physical examination information are interpreted and processed by the general examining physician who is specialized in that examination results. For example, if there is an abnormal internal medicine examination result in the physical examination information u, an internist A is more professional to handle this physical examination report than a surgeon B. that is, the general examining physician A has a higher specialty matching with the physical examination report u.

The workload matching between the physical examination information and the plurality of distribution objects refers to a fact that the workload of the plurality of distribution objects can be equalized based on distribution of physical examination information.

In this embodiment, the information matching model may be obtained in advance by means of iterative training based on the sample physical examination information, the first sample distribution object, and the second sample distribution object, wherein the specialty matching degree between the first sample distribution object and the sample physical examination information is greater than the specialty matching degree between the second sample distribution object and the sample physical examination information. Specifically, during the training process, a first matching degree between the first sample distribution object and the sample physical examination information and a second matching degree between the second sample distribution object and the sample physical examination information may be calculated, and the information matching model is obtained by training with a goal of ensuring a differential between the first matching degree and the second matching degree to be greater than a first preset threshold, and the workload of the first sample distribution object and the workload of the second sample distribution object to be equalized. The specific training process of the information matching model will be described in detail in the subsequent embodiments.

By using the information matching model, the information processing module 72 can give a comprehensive consideration of the matching degree between the plurality of distribution objects and the physical examination information in terms of specialty matching and workload matching, to ensure that the physical examination information can be distributed to the distribution object having a higher specialty matching, while taking account of the workload of each of the plurality of distribution objects, such that the workload of each of the plurality of distribution objects is equalized.

In specific implementation, the information distribution module 73 may use the information processing module 72 to calculate out the matching degree between the physical examination information and each of the plurality of distribution objects. Assuming that there are M distribution objects, the matching degree score between each of the M distribution objects and the physical examination information u may be obtained, and then the information distribution module 73 may determine a target distribution object based on the matching degree between the physical examination information and each of the M distribution objects, and distribute the physical examination information to the target distribution object.

In some embodiments of the present disclosure, the order of execution of the modules is not limited, which may be adjusted according to actual needs.

In this embodiment, there are various implementations for the information distribution module 73 to determine the target distribution object from the plurality of distribution objects.

In one implementation, the matching degree between the physical examination information and the target distribution object may be greater than or equal to a second preset threshold. A specific value of the second preset threshold may be determined according to actual needs, which is not limited in this embodiment.

In another implementation, the matching degree between the physical examination information and the target distribution object may be greater than the matching degree between the physical examination information and other distribution objects. The other distribution objects are distribution objects other than the target distribution object in the plurality of distribution objects. In this implementation, a distribution object with the largest matching degree is determined as the target distribution object.

The physical examination information is represented by u, a set of information of the plurality of distribution objects is represented by $\{d_1, d_2, \ldots, d_N\}$, a value of the function $f(u, d_i) \in R+$ (R+ represents a positive real number) may be configured for measuring the matching degree between the physical examination information u and the information $d_i$ of the plurality of distribution objects, and the larger the value of the function is, the higher the matching degree between the physical examination information u and the distribution object is. In practical application, the physical examination report u is distributed to the target distribution object, wherein the information of the target distribution object may be expressed as $d^* = \max_{d_i}(f(u, d_i))$. That is, the target distribution object may be a distribution object, among the plurality of distribution objects, which has the highest matching degree with the physical examination report. In this embodiment, the function $f(u, d_i)$ represents the information matching model obtained by a pre-training.

By calculating the matching degree between the physical examination information and the plurality of distribution objects by means of the information matching model, the apparatus for distributing physical examination information provided in this embodiment can give a comprehensive consideration of the matching degree between the plurality of distribution objects and the physical examination information in terms of specialty matching and workload matching, to ensure that the physical examination information can be distributed to the distribution object having a higher specialty matching, while taking account of the workload of each of the plurality of distribution objects, such that the workload of each of the plurality of distribution objects is equalized. In this way, the matching between the physical examination information and the plurality of distribution objects is implemented.

In an alternative implementation, the information matching model comprises a semantic vector model and a vector matching model, and the information processing module 72 is specifically configured to:
input the physical examination information and the information of the plurality of distribution objects into the semantic vector model to output a first vector; and
input the first vector into the vector matching model to output the matching degree between the physical examination information and the plurality of distribution objects.

In an alternative implementation, the information processing module 72 is specifically configured to:
splice the physical examination information and the information of the plurality of distribution objects to obtain spliced information, wherein a header of the spliced information employs a marker symbol [CLS], and a separator [SEP] is employed between the physical examination information and the information of the plurality of distribution objects; and
input the spliced information into the semantic vector model to output the first vector.

In an alternative implementation, the information processing module 72 is specifically configured to:
calculate, by the vector matching model, the matching degree between the physical examination information and the plurality of distribution objects based on a formula as below:
score=$W_2^T \sigma(W_1 V_{[cls]} + b_1)$, wherein the score represents the matching degree between the physical examination information and the plurality of distribution objects, the $V_{[cls]}$ represents the first vector, the $W_1$ represents a first mapping matrix of the vector matching model, and the $W_2^T$ represents a transposition of a second mapping matrix $W_2$ of the vector matching model, the $b_1$ represents a bias matrix of the vector matching model, and the $\sigma$ represents an activation function of the vector matching model.

In an alternative implementation, the semantic vector model includes a BERT model.

In an alternative implementation, the vector matching model includes a fully-connected layer network model.

The semantic vector model is configured to map the physical examination information and the information of the plurality of distribution objects into the same vector space. The vector matching model is configured to calculate, in the vector space, the matching degree between the physical examination information and the plurality of distribution objects.

The physical examination information and the information of the plurality of distribution objects are greatly different from each other in terms of word form, but are semantically related to each other. Therefore, the information processing module 72 may map the physical examination information and the information of the plurality of distribution objects into a semantic vector space, wherein semantically related contents are located close to each other in the semantic vector space. Therefore, the matching degree between the physical examination information and the information of the plurality of distribution objects may be measured in the semantic vector space.

The information processing module 72 maps the physical examination information and the information of the plurality of distribution objects into the same vector space by means of the semantic vector model obtained by pre-training, and then further calculates the matching degree between the physical examination information and the plurality of distribution objects in this vector space.

The semantic vector model may be a language model such as a BERT model, an RNN model or an LSTM model, etc. The BERT model is a bi-directional language model in a true sense, and each word may utilize contextual information of this word at the same time. Therefore, the semantic vector model may use the BERT model to obtain a more accurate semantic vector to further improve the matching accuracy.

In this embodiment, the semantic vector model is obtained by training by means of the BERT model. In an alternative implementation, the information processing module 72 may first splice the physical examination information and the information of the plurality of distribution objects to obtain spliced information, wherein a header of the spliced information employs a marker symbol [CLS], and a separator [SEP] is employed between the physical examination information and the information of the plurality of distribution objects. Next, the information processing module 72 inputs the spliced information into the semantic vector model to output the first vector.

In specific implementation, the information processing module 72 may first convert, by using techniques such as word embedding, the physical examination information and the information of the plurality of distribution objects in text form to obtain a word vector. Referring to FIG. 3, "word i" represents the $i^{th}$ word in the corresponding text (the physical examination information or the information of the plurality of distribution objects), and the text "word i" corresponding to each word is transformed into a vector Ei or Ei' by means of word embedding, etc. Ei represents the word vector of the physical examination information, and Ei' represents the word vector of the information of the plurality of distribution objects. Next, Ei and Ei' may be used as initialization vectors, and the physical examination information and the information of the plurality of distribution objects in the form of word vector are spliced by means of the marker symbol [CLS] and the separator [SEP] to obtain the spliced information. Specifically, the marker symbol [CLS] may be added to the header of the spliced information, and the separator [SEP] may be added between the physical examination information u and the information d of the plurality of distribution objects. Next, the spliced information may be inputted as a whole into the semantic vector model such as the BERT model to obtain the first vector.

As the head of the spliced information, the marker symbol [CLS] represents that an output vector V[cls] corresponding to this symbol may be used as semantic representation or semantic vector of the spliced information. Semantic information of each word in the spliced information may be more "fairly" integrated by means of the marker symbol [CLS]. The separator [SEP] is configured for distinguishing the physical examination information in the spliced information from the information of the plurality of distribution objects.

As shown in FIG. 3, the first vector V[cls] is an output result of the semantic vector model, and the first vector V[cls] contains the physical examination information u and the information d of the plurality of distribution objects. In some embodiments, the first vector V[cls] represents a vector corresponding to the inputted physical examination information and the information of the plurality of distribution objects. When the semantic vector model employs the BERT model, dimensionality of the first vector V[cls] is 768 dimensions. In this implementation, a vector dimension of the BERT model is 768 dimensions by default. Of course, a vector in the BERT model may also have other dimensions, which is not limited in this embodiment. Vi or Vi' in FIG. 3 represents a vector outputted after the "word i" is processed by the semantic vector model.

In specific implementation, the information processing module 72 may input an information pair comprising the physical examination information and the information of each of the plurality of distribution objects into the semantic vector model obtained by pre-training, to obtain the first vector corresponding to the inputted physical examination information and the information of the plurality of distribution objects. In this way, the physical examination information and the information of each of the plurality of distribution objects can be mapped into the same vector space by means of the semantic vector model.

In an alternative implementation, the vector matching model may employ a fully-connected layer network model. It is to be noted that the vector matching model is not limited to the fully-connected layer network model. Any network model that can transform an input vector into a scalar may be used as the vector matching model.

In an alternative implementation, the vector matching model may calculate the matching degree between the physical examination information and the plurality of distribution objects based on a formula as below:

score=$W_2^T \sigma(W_1 V_{[cls]} + b_1)$, wherein the score represents the matching degree between the physical examination information and the plurality of distribution objects, the $V_{[cls]}$ represents the first vector, the $W_1$ represents a first mapping matrix of the vector matching model, and the $W_2^T$ represents a transposition of a second mapping matrix $W_2$ of the vector matching model, the $b_1$ represents a bias matrix of the vector matching model, and the $\sigma$ represents an activation function of the vector matching model.

As shown in FIG. 4, the information processing module 72 may input the first vector V[cls] into the vector matching model, and output the matching degree score between the physical examination information and the plurality of distribution objects. $x_i$ in FIG. 4 represents a value of the $i^{th}$ dimension in the first vector V[cls]. When the semantic vector model employs the BERT model, $W_1$ may represent a matrix of 384*768, and $W_2$ and $b_1$ may represent matrices of 384*1.

Parameters of the semantic vector model and parameters such as matrices W1, W2 and b1 in the vector matching model may be obtained by joint training. Parameters in a pre-trained model may be used as initial values of the parameters of the semantic vector model, and initial values of the matrices W1, W2 and b1 in the vector matching model may be obtained by means of random initialization. For example, the model is pre-trained using a mass of data to obtain the parameters in the pre-trained model, and then these parameters are finely adjusted on specific tasks. Specific training processes of the semantic vector model and the vector matching model will be described in detail in subsequent embodiments.

In this embodiment, the information processing module 72 maps the physical examination information and the information of the plurality of distribution objects into the same vector space by means of the semantic vector model, calculates the matching degree between the physical examination information and each of the plurality of distribution objects in the vector space, and then distributes the physical examination information to the appropriate distribution object according to the matching degree.

In an alternative implementation, the apparatus also includes a model training module, which is specifically configured to:

obtain a plurality of training sample pairs, each of the plurality of training sample pairs being a first sample pair or a second sample pair, the first sample pair comprising sample physical examination information and information of a first sample distribution object, the second sample pair comprising the sample physical examination information and information of a second sample distribution object, wherein the matching degree of the first sample pair is greater than that of the second sample pair, the sample physical examination information comprises abnormal sample physical examination information, information of a sample distribution object comprises specialty information of the sample distribution object, and the sample distribution object is the first sample distribution object or the second sample distribution object;

input the training sample pair into a model to be trained to obtain the matching degree of the training sample pair; and train the model to be trained according to the matching degree of the first sample pair, the matching degree of the second sample pair, workload information of the sample physical examination information, and workload information of each of the sample distribution objects, to determine the model to be trained after training as the information matching model.

In an alternative implementation, the model training module is specifically configured to:

train the model to be trained with a goal of ensuring a differential between the matching degree of the first sample pair and the matching degree of the second sample pair to be greater than a first preset threshold, and a first parameter of each of the sample distribution objects to be equal, wherein the first preset threshold is greater than zero, the first parameter is configured for characterizing the workload of each of the sample distribution objects, and the first parameter is determined by the workload information of the sample physical examination information;

calculate the differential between the matching degree of the first sample pair and the matching degree of the second sample pair, and determine a first loss portion according to the differential and the first preset threshold;

determine a second loss portion according to a second parameter of the sample physical examination information, a third parameter of the plurality of sample distribution objects, and the first parameter of each of the sample distribution objects, wherein the second parameter is configured for characterizing the workload of the sample physical examination information, and the third parameter is configured for characterizing a number of the plurality of sample distribution objects;

perform a weighted summation of the first loss portion and the second loss portion to obtain a loss function; and train the model to be trained with a goal of minimizing the loss function.

In an alternative implementation, the model training module is specifically configured to:

determine the first loss portion based on a formula as below:

$L1 = \Sigma_{(u_j, d_{ij})} \Sigma_{(u_j, d_{il})}[\text{score}(u_j, d_{il}) + \gamma - \text{score}(u_j, d_{ij})]_+$, wherein the L1 represents the first loss portion, the $u_j$ represents the sample physical examination information, the $d_{ij}$ represents the information of the first sample distribution object, the $d_{il}$ represents the information of the second sample distribution object, the $(u_j, d_{ij})$ represents the first sample pair, the $(u_j, d_{il})$ represents the second sample pair, the $\text{score}(u_j, d_{il})$ represents the matching degree of the second sample pair, the $\text{score}(u_j, d_{ij})$ represents the matching degree of the first sample pair, and the $\gamma$ represents the first preset threshold;

determine the second loss portion based on a formula as below:

$L2 = \Sigma_{i=1}^{M}(N/M - h_i)^2$, wherein the L2 represents the second loss portion, the N represents the second parameter, the M represents the third parameter, and the $h_i$ represents the first parameter of the sample distribution object i; and determine the loss function based on a formula as below: $L = L1 + \beta L2$, wherein the L represents the loss function, and the $\beta$ represents a harmonic parameter.

In an alternative implementation, when the information matching model comprises the semantic vector model and the vector matching model, the model to be trained comprises a first model to be trained and a second model to be trained, and the model training module is specifically configured to:

input the training sample pair into the first model to be trained to obtain a vector of the training sample pair;

input the vector of the training sample pair into the second model to be trained to obtain the matching degree of the training sample pair; and train the first model to be trained and the second model to be trained according to the matching degree of the first sample pair, the matching degree of the second sample pair, the workload information of the sample physical examination information, and the workload information of each of the sample distribution objects, to determine the first model to be trained after training as the semantic vector model and determine the second model to be trained after training as the vector matching model.

The sample physical examination information may be, for example, a sample physical examination report in which a single examination result has been completed but it needs to provide a general examination result. The sample physical examination information may include examination results (for example, electrocardiogram examination results include sinus rhythm, etc.) of a series of physical examination items (such as general examination, internal medicine examination, electrocardiogram, and head CT, etc.).

In this embodiment, the sample physical examination information may include abnormal sample physical examination information, and the abnormal sample physical examination information may include abnormal examination results or abnormal physical examination items, etc. Specific contents of the abnormal sample physical examination information are not limited in this embodiment.

The sample distribution object may be, for example, a general examining physician. The information of the plurality of sample distribution objects may include specialty information of the plurality of sample distribution objects. The specialty information may include descriptions and introductions of the general examining physician's graduate institution, specialized subject, years of working, and adept examination items, etc. However, this embodiment does not limit the specific contents of the specialty information. For example, the specialty information may be as below: Dr. A, graduated from XX, . . . , worked for XX years, . . . , specializing in internal medicine. . . .

In this embodiment, the first sample distribution object may be a sample distribution object having specialty matching with the sample physical examination information. That is, the specialty information of the first sample distribution object matches the abnormal sample physical examination information in the sample physical examination information. The second sample distribution object may be a sample distribution object having no specialty matching with the sample physical examination information. That is, the specialty information of the second sample distribution object does not match the abnormal sample physical examination information in the sample physical examination information. In the process of obtaining the training sample pair, the first sample distribution object and the second sample distribution object may be, for example, artificially specified based on the sample physical examination information and the information of the sample distribution object. For example, if the specialty matching degree of the first sample distribution object is greater than the specialty matching degree of the second sample distribution object, the first sample distribution object may be considered as a sample distribution object having specialty matching with the sample physical examination information, and the second sample distribution object may be considered as a sample distribution object having no specialty matching with the sample physical examination information.

The first sample pair $(u_j, d_{ij})$ includes the sample physical examination information $u_j$ and information $d_{ij}$ (wherein subscript ij ∈ [1, M], and M represents a total number of sample distribution objects) of the first sample distribution object, and the second sample pair $(u_j, d_{il})$ includes the sample physical examination information $u_j$ and information $d_{il}$ (wherein subscript ij ∈ [1, M], and ij≠il) of the second sample distribution object. The matching degree of the first sample pair $(u_j, d_{ij})$ may be greater than the matching degree of the second sample pair $(u_j, d_{il})$. That is, the sample physical examination information has a higher specialty matching with the first sample distribution object.

The workload information of the sample physical examination information may be determined, for example, by number of copies of the sample physical examination reports contained in the sample physical examination information, and also may be determined by number of words in the abnormal examination results, etc. However, this embodiment is not limited thereto.

The workload information of the sample distribution object may be determined by the workload of the sample physical examination information having specialty matching with the sample distribution object, for example, the number of the sample physical examination information having specialty matching with the sample distribution object.

The first model to be trained may be a language model such as a BERT model, an RNN model, or an LSTM. The BERT model is a bi-directional language model in a true sense, and each word may utilize contextual information of this word at the same time. Therefore, the first model to be trained may use the BERT model to obtain a more accurate semantic vector to further improve the matching accuracy.

The second model to be trained may employ a fully-connected layer network model. It is to be noted that the second model to be trained is not limited to the fully-connected layer network model. Any network model that can transform an input vector into a scalar may be used as the second model to be trained.

In specific implementation, the model training module may input a training sample pair into the first model to be trained to obtain a vector corresponding to the inputted training sample pair, and then inputs the vector of the training sample pair into the second model to be trained to obtain the matching degree corresponding to the inputted training sample pair. In this way, the matching degrees of all the training sample pairs can be obtained, including the matching degree score $(u_j, d_{ij})$ of the first sample pair $(u_j, d_{ij})$ and the matching degree score $(u_j, d_{il})$ of the second sample pair $(u_j, d_{il})$. Next, the first model to be trained and the second model to be trained may be trained based on the matching degree of the first sample pair, the matching degree of the second sample pair, the workload information of the sample physical examination information, and the workload information of each of the sample distribution objects.

In an alternative implementation, the model training module may train the model to be trained with a goal of ensuring a differential between the matching degree score $(u_j, d_{ij})$ of the first sample pair and the matching degree score $(u_j, d_{il})$ of the second sample pair to be greater than a first preset threshold γ, and a first parameter of each of the sample distribution objects to be equal. The first preset threshold is greater than zero, and the sample distribution object is the first sample distribution object or the second sample distribution object. The first parameter is configured for characterizing the workload of each of the sample distribution objects, and the first parameter is determined by the workload information of the sample physical examination information. For example, the first parameter may be the workload of the sample physical examination information having specialty matching with the sample distribution object.

In some embodiments, "equal" may be exactly equal or the differential is less than a certain threshold, which may be set as needed.

In practical application, the model training module may determine a first training objective where the matching degree score$(u_j, d_{ij})$ of the first sample pair is at least higher by the first preset threshold γ than the matching degree score$(u_j, d_{il})$ of the second sample pair, that is, score$(u_j, d_{ij})$>score$(u_j, d_{il})$+γ, wherein il ∈ [1, M], ij ∈ [1, M] and ij≠il. The first preset threshold is greater than zero. For example, the first preset threshold may be set to 1, but its specific value may be set according to the actual situations, and this embodiment is not limited thereto.

In specific implementation, the model training module may determine the first loss portion based on a formula as below:

$L1 = \Sigma_{(u_j, d_{ij})} \Sigma_{(u_j, d_{il})} [\text{score}(u_j, d_{il}) + \gamma - \text{score}(u_j, d_{ij})]_+$,
wherein the L1 represents the first loss portion, the $u_j$ represents the sample physical examination information, the $d_{ij}$ represents the information of the first sample distribution object, the $d_{il}$ represents the information of the second sample distribution object, the $(u_j, d_{ij})$ represents the first sample pair, the $(u_j, d_{il})$ represents the second sample pair, the score$(u_j, d_{il})$ represents the matching degree of the second sample pair, the score$(u_j, d_{ij})$ represents the matching degree of the first sample pair, and the γ represents the first preset threshold. If a≤0, [a]+=0; otherwise [a]+=a.

In this embodiment, the model training module may determine a second training objective where the first parameter of each of the sample distribution objects is equal, or the model training module may determine the second training objective where a differential between the first parameter of each of the sample distribution objects and an average workload is minimum, such that the model obtained by training can equalize the workload of each of the plurality of distribution objects.

In specific implementation, the model training module may first calculate a ratio of the second parameter to the third parameter, and then determines the second loss portion based on a differential between the first parameter and the ratio.

Assuming that the workload of each piece of sample physical examination information u is $u\_c_i$, where i ∈ [1, k] and k represents the total number of pieces of sample physical examination information, the total workload (i.e., the second parameter) is $u\_c = \Sigma_1^k u_{c_i}$, the average workload is $\overline{u\_c} = u\_c/M$, and M represents the number of sample distribution objects, and serves as a third parameter. Assuming that the sample physical examination information matching the sample distribution object j includes $\{u_{j1}, \ldots, u_{jh}\}$, imbalance of workload of the sample distribution object may be represented by $V_j = (\overline{u\_c} - \Sigma_{l=1}^h u\_c_{jl})^2$, wherein $\Sigma_{l=1}^h u\_c_{jl}$ represents the workload (i.e., the first parameter) of the sample physical examination information having specialty matching with the sample distribution object j.

For a simplified description, in this embodiment it is assumed that the workload of each piece of physical examination information is the same, and is set to 1, i.e., $u_{c_i} = 1$, i ∈ [1, k]. In this case, $$\overline{u\_c} = \frac{N}{M},$$

wherein N represents the total number of pieces of sample physical examination information, i.e., the second parameter, and M represents the number of sample distribution objects, i.e., the third parameter. Because $u_{c_i}=1$ and $i \in [1, k]$, the first parameter of the sample distribution object j is $\Sigma_{l=1}^{h_j} u\_c_{ji} = h_j$, and thus $$V_j = \left(\frac{N}{M} - h_j\right)^2.$$

In specific implementation, the model training module may determine the second loss portion based on a formula as below:

$L2 = \Sigma_{i=1}^{M}(N/M - h_i)^2$, wherein the L2 represents the second loss portion, the N represents the second parameter, the M represents the third parameter, and the $h_i$ represents the first parameter of the sample distribution object i.

According to the calculation formula of the second loss portion, it can be known that when the number of pieces of sample physical examination information processed by each of the sample distribution objects is an average number N/M, the workload of each of the sample distribution objects is the same, i.e., the average workload. In this case, the loss of workload balance is the minimum, i.e., zero. However, the loss increases when the number of pieces of sample physical examination information processed by each of the sample distribution objects differs greatly.

In specific implementation, the model training module may determine the loss function based on a formula as below:

$L = L1 + \beta L2$, wherein L represents the loss function, and $\beta$ represents a harmonic parameter.

In specific implementation, the model training module may minimize the loss function by using batch gradient descent to learn the model parameters.

In this embodiment, the model training module measures the loss of specialty matching degree between the sample physical examination information and each of the sample distribution objects by means of the first loss portion, and measures the loss of workload balance of each sample distribution object by means of the second loss portion. When the matching degree score($u_j$, $d_{ij}$) of the first sample pair is at least higher by $\gamma$ than the matching degree score($u_j$, $d_{il}$) of the second sample pair and the workload (i.e., the first parameter) processed by each of the plurality of distribution objects is the same, the loss function L is minimized to zero.

As can be seen from the formula of the loss function L, if each piece of physical examination information is distributed to a distribution object having the highest specialty matching degree, this will cause a consequence that some distribution objects process a lot of physical examination information but some distribution objects process very little physical examination information. In this case, the first loss portion is smaller but the second loss portion is larger. In a model training process, the total loss function L may be minimized by adjusting the parameters, such that some physical examination information may be distributed to a distribution object having a higher specialty matching degree (such as the second or third highest specialty matching degree), to ensure the workload of the distribution objects to be balanced.

The information matching model may be obtained by training the model to be trained by the model training module using the above loss function. The semantic vector model and the vector matching model may be obtained by training the first model to be trained and the second model to be trained using the above loss function. The matching degree between new physical examination information and each of the plurality of distribution objects can be calculated by using the trained information matching model or the semantic vector model and the vector matching model, such that the target distribution object having a higher specialty matching degree and a balanced workload can be selected from the plurality of distribution objects.

In this embodiment, by constructing the semantic vector model and the vector matching model, the physical examination information and the information of the plurality of distribution objects are mapped into the same vector space, and the target distribution object is determined in this vector space according to the specialty matching degree and the workload balance degree, and then the physical examination information is distributed to the target distribution object. In this solution, it is taken account of the specialty matching degree between the physical examination information and the plurality of distribution objects as well as the workload balance of each of the plurality of distribution objects. Compared with the traditional method, in this solution, the physical examination information can be distributed to a distribution target having a higher matching degree, while the workload of each of the plurality of distribution objects can be reasonably distributed, to achieve a workload balance for each of the plurality of distribution objects.

With regard to the apparatus in the above embodiments, specific implementation manners for executing operations by modules thereof have been described in detail in the embodiments related to the method, for example, implemented by means of software, hardware or firmware, and thus are not elaborated herein.

Figure 8:
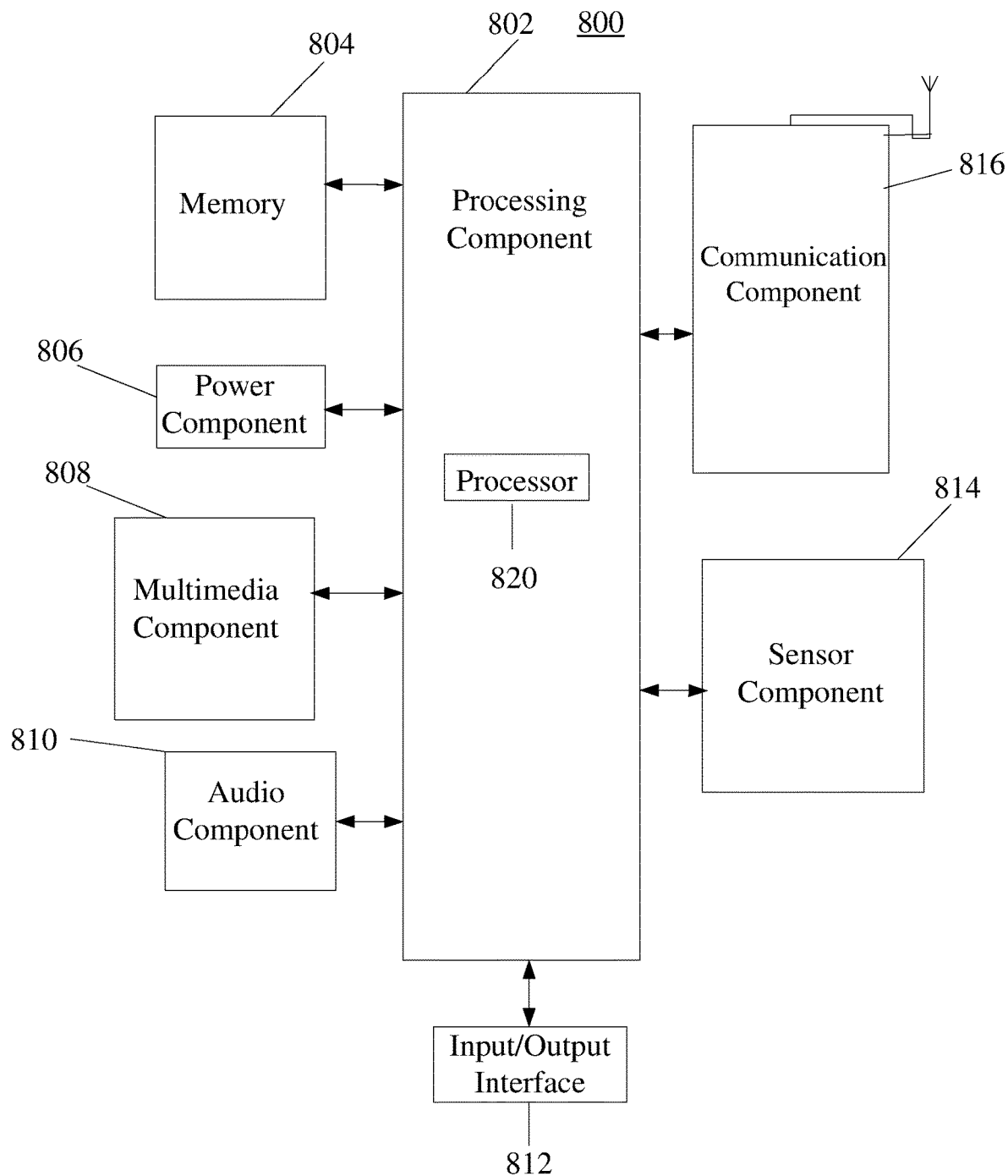
FIG. 8 illustrates a block diagram of an electronic device according to an exemplary embodiment.

FIG. 8 illustrates a block diagram of an electronic device 800 according to the present disclosure. For example, the electronic device 800 may be a mobile telephone, a computer, a digital broadcasting terminal, a message transceiver device, a games console, a tablet device, a medical device, a fitness facility, a PDA (personal digital assistant), and the like.

Referring to FIG. 8, the electronic device 800 may include one or more of the following components: a processing component 802, a memory 804, a power component 806, a multimedia component 808, an audio component 810, an input/output (I/O) interface 812, a sensor component 814, and a communication component 816.

The processing component 802 typically controls overall operations of the electronic device 800, such as the operations associated with display, telephone calls, data communications, camera operations, and recording operations. The processing component 802 may include one or more processors 820 to execute instructions to perform all or part of the steps in the method for distributing physical examination information according to any one of the above embodiments. Moreover, the processing component 802 may include one or more modules which facilitate the interaction between the processing component 802 and other components. For instance, the processing component 802 may include a multimedia module to facilitate the interaction between the multimedia component 808 and the processing component 802.

The memory 804 is configured to store various types of data to support the operation of the device 800. Examples of such data include instructions for any applications or methods operated on the electronic device 800, contact data, phonebook data, messages, pictures, video, etc. The memory 804 may be implemented using any type of volatile or non-volatile memory devices, or a combination thereof, such as a static random access memory (SRAM), an erasable programmable read-only memory (EPROM), a programmable read-only memory (PROM), a read-only memory (ROM), a magnetic memory, a flash memory, a magnetic or optical disk.

The power component 806 provides power to various components of the electronic device 800. The power component 806 may include a power management system, one or more power sources, and any other components associated with the generation, management, and distribution of power in the electronic device 800.

The multimedia component 808 includes a screen providing an output interface between the electronic device 800 and the user. In some embodiments, the screen may include a liquid crystal display (LCD) and a touch panel (TP). If the screen includes the touch panel, the screen may be implemented as a touch screen to receive input signals from the user. The touch panel includes one or more touch sensors to sense touches, swipes, and gestures on the touch panel. The touch sensors may not only sense a boundary of a touch or swipe action, but also sense a period of time and a pressure associated with the touch or swipe action. In some embodiments, the multimedia component 808 includes a front camera and/or a rear camera. The front camera and the rear camera may receive an external multimedia datum while the device 800 is in an operation mode, such as a photographing mode or a video mode. Each of the front camera and the rear camera may be a fixed optical lens system or have focus and optical zoom capability.

The audio component 810 is configured to output and/or input audio signals. For example, the audio component 810 includes a microphone ("MIC") configured to receive an external audio signal when the electronic device 800 is in an operation mode, such as a call mode, a recording mode, and a voice recognition mode. The received audio signal may be further stored in the memory 804 or transmitted via the communication component 816. In some embodiments, the audio component 810 further includes a speaker to output audio signals.

The I/O interface 812 provides an interface between the processing component 802 and peripheral interface modules, such as a keyboard, a click wheel, buttons, and the like. The buttons may include, but are not limited to, a home button, a volume button, a starting button, and a locking button.

The sensor component 814 includes one or more sensors to provide status assessments of various aspects of the electronic device 800. For instance, the sensor component 814 may detect an open/closed status of the electronic device 800, relative positioning of components, e.g., the display and the keypad, of the electronic device 800, a change in position of the electronic device 800 or a component of the electronic device 800, a presence or absence of user contact with the electronic device 800, an orientation or an acceleration/deceleration of the electronic device 800, and a change in temperature of the electronic device 800. The sensor component 814 may include a proximity sensor configured to detect the presence of nearby objects without any physical contact. The sensor component 814 may also include a light sensor, such as a CMOS or CCD image sensor, for use in imaging applications. In some embodiments, the sensor component 814 may also include an accelerometer sensor, a gyroscope sensor, a magnetic sensor, a pressure sensor, or a temperature sensor.

The communication component 816 is configured to facilitate communication, wired or wirelessly, between the electronic device 800 and other devices. The electronic device 800 can access a wireless network based on a communication standard, such as WiFi, carrier networks (such as 2G, 3G, 4G, or 5G), or a combination thereof. In one exemplary embodiment, the communication component 816 receives a broadcast signal or broadcast associated information from an external broadcast management system via a broadcast channel. In one exemplary embodiment, the communication component 816 further includes a near field communication (NFC) module to facilitate short-range communications. For example, the NFC module may be implemented based on a radio frequency identification (RFID) technology, an infrared data association (IrDA) technology, an ultra-wideband (UWB) technology, a Bluetooth (BT) technology, and other technologies.

In exemplary embodiments, the electronic device 800 may be implemented with one or more application specific integrated circuits (ASICs), digital signal processors (DSPs), digital signal processing devices (DSPDs), programmable logic devices (PLDs), field programmable gate arrays (FPGAs), controllers, micro-controllers, microprocessors, or other electronic components, for performing the method for distributing physical examination information according to any one embodiment.

Figure 9:
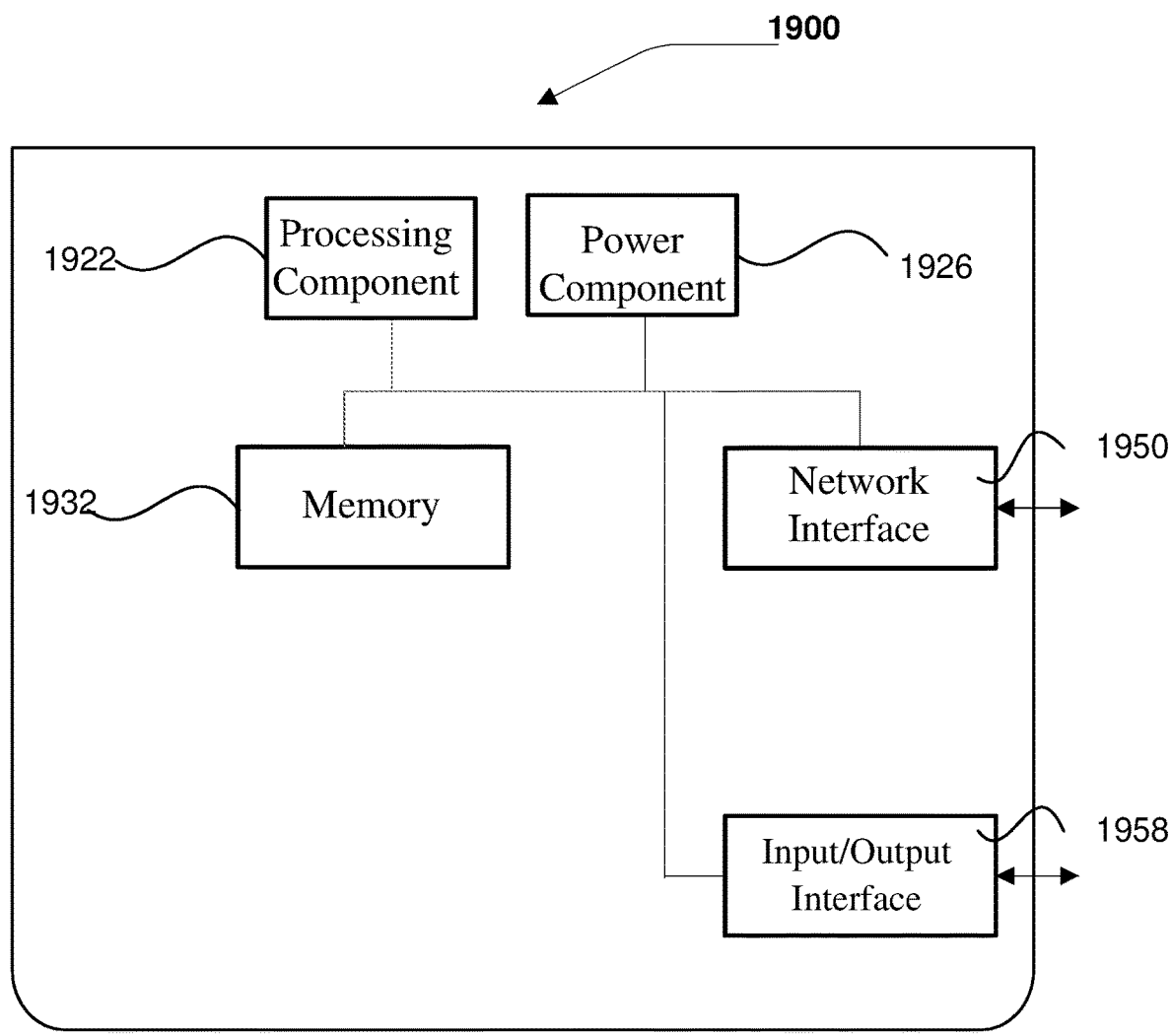
FIG. 9 illustrates a block diagram of another electronic device according to an exemplary embodiment.

As shown in FIG. 9, in exemplary embodiments, the processing component 1922 performs the above method for distributing physical examination information, receives, by means of an input interface 1958, information inputted by the user, such as the physical examination information and the information of the plurality of distribution objects, and outputs a distribution result by means of an output interface 1958, for example, distributes the physical examination information to the target distribution object.

In exemplary embodiment, after the matching degree between the physical examination information and each of the plurality of distribution objects is determined, each of the plurality of distribution objects is sorted according to the matching degree, and a sorting result is outputted via the output interface 1958. For example, the user can select each of the plurality of distribution objects via a user interaction interface, or can edit the sequence, such as adjusting an arrangement number sequence, etc.

In exemplary embodiments, there is also provided a non-transitory computer-readable storage medium including instructions, such as a memory 804 including instructions. Such instructions may be executed by the processor 820 of the electronic device 800 to perform the method for distributing physical examination information according to any one of the above embodiments. For example, the non-transitory computer-readable storage medium may be a ROM, a random access memory (RAM), a CD-ROM, a magnetic tape, a floppy disc, an optical data storage device, and the like.

In exemplary embodiments, there is also provided a computer program product, which includes a readable program code that can be executed by the processor 820 of the device 800 to perform the method for distributing physical examination information according to any one of the above embodiments. Alternatively, the program code may be stored in a storage medium of the device 800, and the storage medium may be a non-transitory computer-readable storage medium. For example, the non-transitory computer-readable storage medium may be a ROM, a random access memory (RAM), a CD-ROM, a magnetic tape, a floppy disc, an optical data storage device, and the like.

FIG. 9 illustrates a block diagram of an electronic device 1900 according to the present disclosure. For example, the electronic device 1900 may be provided as a server.

Referring to FIG. 9, the electronic device 1900 includes a processing component 1922, and the processing component 1922 further includes one or more processors, and memory resource represented by a memory 1932 to store instructions such as an application program executable by the processing component 1922. The application program stored in the memory 1932 may include one or more modules, each of which corresponds to a set of instructions. In addition, the processing component 1922 is configured to execute the instructions to perform the method for distributing physical examination information according to any one of the above embodiments.

The electronic device 1900 may also include one power component 1926 configured to execute the power management of the electronic device 1900, one wired or wireless network interface 1950 configured to connect the electronic device 1900 to the network, and one input/output (I/O) interface 1958. The electronic device 1900 can operate an operating system stored in the memory 1932, for example, WindowsServer™, MacOSX™, Unix™, Linux™, FreeBSD™ or other similar operating systems.

"One embodiment", "embodiments" or "one or more embodiments" herein means that the particular features, structures or characteristics described in combination with the embodiments are included in at least one embodiment of the present disclosure. Furthermore, it is to be noted that the term "in one embodiment" herein does not necessarily refer to the same embodiment.

Many details are discussed in the specification provided herein. However, it is to be understood that the embodiments of the present disclosure can be implemented without these specific details. In some examples, the well-known methods, structures and technologies are not shown in detail so as to avoid an unclear understanding of the description.

In the claims, no reference mark between round brackets shall impose restriction on the claims. The word "comprise" does not exclude the presence of a component or step not listed in the claims. The wording "a" or "one" in front of a component does not exclude the presence of a plurality of such components. The present disclosure may be implemented by means of hardware comprising a plurality of different components and by means of a suitably programmed computer. In the unit claim listing a plurality of devices, some of these devices may be embodied in the same hardware. The wordings "first", "second", and "third", etc. do not denote any order. These wordings can be construed as naming.

Finally, it should be noted that the foregoing embodiments are merely intended for describing the technical solutions of the present disclosure, but not for limiting the present disclosure. Although the present disclosure is described in detail with reference to the foregoing embodiments, persons of ordinary skill in the art should understand that they may still make modifications to the technical solutions described in the foregoing embodiments or make equivalent replacements to some or all technical features thereof, without departing from the spirit or scope of the technical solutions of the embodiments of the present disclosure.

The invention claimed is:

1. A method for distributing physical examination information, comprising:

obtaining physical examination information and information of a plurality of distribution objects, the physical examination information comprising abnormal physical examination information and workload information of the physical examination information, and the information of the plurality of distribution objects comprising specialty information and workload information of the plurality of distribution objects;

inputting the physical examination information and the information of the plurality of distribution objects into an information matching model obtained by pre-training to obtain a matching degree between the physical examination information and the plurality of distribution objects, wherein the information matching model is configured to calculate the matching degree between the physical examination information and the plurality of distribution objects according to the abnormal physical examination information, the workload information of the physical examination information, and the specialty information and the workload information of the plurality of distribution objects; and determining a target distribution object from the plurality of distribution objects according to the matching degree between the physical examination information and each of the plurality of distribution objects, and distributing the physical examination information to the target distribution object;

wherein the information matching model comprises a semantic vector model and a vector matching model, and the step of inputting the physical examination information and the information of the plurality of distribution objects into an information matching model obtained by pre-training to obtain a matching degree between the physical examination information and the plurality of distribution objects comprises:

inputting the physical examination information and the information of the plurality of distribution objects into the semantic vector model to output a first vector; and inputting the first vector into the vector matching model to output the matching degree between the physical examination information and the plurality of distribution objects;

wherein the step of inputting the first vector into the vector matching model to output the matching degree between the physical examination information and the plurality of distribution objects comprises:

calculating, by the vector matching model, the matching degree between the physical examination information and the plurality of distribution objects based on a formula as below:

score=$W_2^T \sigma(W_1 V_{[cls]}+b_1)$, wherein the score represents the matching degree between the physical examination information and the plurality of distribution objects, the $V_{[cls]}$ represents the first vector, the $W_1$ represents a first mapping matrix of the vector matching model, and the $W_2^T$ represents a transposition of a second mapping matrix $W_2$ of the vector matching model, the $b_1$ represents a bias matrix of the vector matching model, and the $\sigma$ represents an activation function of the vector matching model.

2. The method for distributing physical examination information according to claim 1, wherein the step of inputting the physical examination information and the information of the plurality of distribution objects into the semantic vector model to output a first vector comprises:

splicing the physical examination information and the information of the plurality of distribution objects to obtain spliced information, wherein a header of the spliced information employs a marker symbol [CLS], and a separator [SEP] is employed between the physical examination information and the information of the plurality of distribution objects; and inputting the spliced information into the semantic vector model to output the first vector.

3. The method for distributing physical examination information according to claim 1, wherein the semantic vector model comprises a BERT model.

4. The method for distributing physical examination information according to claim 1, wherein the vector matching model comprises a fully-connected layer network model.

5. The method for distributing physical examination information according to claim 1, wherein the matching degree between the physical examination information and the target distribution object is greater than or equal to a second preset threshold value; or the matching degree between the physical examination information and the target distribution object is greater than the matching degree between the physical examination information and another distribution object, wherein the other distribution object is a distribution object other than the target distribution object in the plurality of distribution objects.

6. A non-transitory computer-readable storage medium, wherein a code in the non-transitory computer-readable storage medium is executable by a processor of an electronic device, whereby the electronic device is configured to perform the method for distributing physical examination information according to claim 1.

7. A non-transitory computer program product, storing a computer program, wherein the computer program is executable by a processor, whereby the method for distributing physical examination information according to claim 1 is implemented.

8. A method for distributing physical examination information, comprising:

obtaining physical examination information and information of a plurality of distribution objects, the physical examination information comprising abnormal physical examination information and workload information of the physical examination information, and the information of the plurality of distribution objects comprising specialty information and workload information of the plurality of distribution objects;

inputting the physical examination information and the information of the plurality of distribution objects into an information matching model obtained by pre-training to obtain a matching degree between the physical examination information and the plurality of distribution objects, wherein the information matching model is configured to calculate the matching degree between the physical examination information and the plurality of distribution objects according to the abnormal physical examination information, the workload information of the physical examination information, and the specialty information and the workload information of the plurality of distribution objects; and determining a target distribution object from the plurality of distribution objects according to the matching degree between the physical examination information and each of the plurality of distribution objects, and distributing the physical examination information to the target distribution object;

wherein before the step of inputting the physical examination information and the information of the plurality of distribution objects into an information matching model obtained by pre-training to obtain a matching degree between the physical examination information and the plurality of distribution objects, the method further comprises:

obtaining a plurality of training sample pairs, each of the plurality of training sample pairs being a first sample pair or a second sample pair, the first sample pair comprising sample physical examination information and information of a first sample distribution object, the second sample pair comprising the sample physical examination information and information of a second sample distribution object, wherein the matching degree of the first sample pair is greater than that of the second sample pair, the sample physical examination information comprises abnormal sample physical examination information, information of a sample distribution object comprises specialty information of the sample distribution object, and the sample distribution object is the first sample distribution object or the second sample distribution object;

inputting the training sample pair into a model to be trained to obtain the matching degree of the training sample pair; and training the model to be trained according to the matching degree of the first sample pair, the matching degree of the second sample pair, workload information of the sample physical examination information, and workload information of each of the sample distribution objects, to determine the model to be trained after training as the information matching model.

9. The method for distributing physical examination information according to claim 8, wherein the training the model to be trained according to the matching degree of the first sample pair, the matching degree of the second sample pair, workload information of the sample physical examination information, and workload information of each of the sample distribution objects, to determine the model to be trained after training as the information matching model comprises:

training the model to be trained with a goal of ensuring a differential between the matching degree of the first sample pair and the matching degree of the second sample pair to be greater than a first preset threshold, and a first parameter of each of the sample distribution objects to be equal, wherein the first preset threshold is greater than zero, the first parameter is configured for characterizing the workload of each of the sample distribution objects, and the first parameter is determined by the workload information of the sample physical examination information.

10. The method for distributing physical examination information according to claim 9, wherein the step of training the model to be trained with a goal of ensuring a differential between the matching degree of the first sample pair and the matching degree of the second sample pair to be greater than a first preset threshold, and a first parameter of each of the sample distribution objects to be equal comprises:

calculating the differential between the matching degree of the first sample pair and the matching degree of the second sample pair, and determining a first loss portion according to the differential and the first preset threshold;

determining a second loss portion according to a second parameter of the sample physical examination information, a third parameter of the plurality of sample distribution objects, and the first parameter of each of the sample distribution objects, wherein the second parameter is configured for characterizing the workload of the sample physical examination information, and the third parameter is configured for characterizing number of the plurality of sample distribution objects;

performing a weighted summation of the first loss portion and the second loss portion to obtain a loss function; and training the model to be trained with a goal of minimizing the loss function.

11. The method for distributing physical examination information according to claim 10, wherein the first loss portion is determined based on a formula as below:

$L1 = \Sigma(u_j, d_{ij}) \Sigma(u_j, d_{il})$ [score $(u_j, d_{il}) + \gamma$ – score$(u_j, d_{ij})]_+$, wherein the L1 represents the first loss portion, the $u_j$ represents the sample physical examination information, the $d_{ij}$ represents the information of the first sample distribution object, the du represents the information of the second sample distribution object, the $(u_j, d_{ij})$ represents the first sample pair, the $(u_j, d_{il})$ represents the second sample pair, the score $(u_j, d_{il})$ represents the matching degree of the second sample pair, the score $(u_j, d_{ij})$ represents the matching degree of the first sample pair, and the $\gamma$ represents the first preset threshold; and the second loss portion is determined based on a formula as below:

$L2 = \Sigma_{i=1}^{M}(N/M - h_i)^2$, wherein the L2 represents the second loss portion, the N represents the second parameter, the M represents the third parameter, and the $h_i$ represents the first parameter of the sample distribution object i; and the loss function is determined based on a formula as below:

$L = L1 + \beta L2$, wherein the L represents the loss function, and the $\beta$ represents a harmonic parameter.

12. The method for distributing physical examination information according to claim 8, wherein when the information matching model comprises a semantic vector model and a vector matching model, the model to be trained comprises a first model to be trained and a second model to be trained, the step of inputting the training sample pair into the model to be trained to obtain the matching degree of the training sample pair comprises:

inputting the training sample pair into the first model to be trained to obtain a vector of the training sample pair; and inputting the vector of the training sample pair into the second model to be trained to obtain the matching degree of the training sample pair;

wherein the training the model to be trained according to the matching degree of the first sample pair, the matching degree of the second sample pair, workload information of the sample physical examination information, and workload information of each of the sample distribution objects, to determine the model to be trained after training as the information matching model comprises:

training the first model to be trained and the second model to be trained according to the matching degree of the first sample pair, the matching degree of the second sample pair, the workload information of the sample physical examination information, and the workload information of each of the sample distribution objects, to determine the first model to be trained after training as the semantic vector model and determine the second model to be trained after training as the vector matching model.

13. An electronic device, comprising:

a processor, and a memory configured to store instructions executable by the processor;

wherein the processor is configured to execute the instructions to implement the operations comprising:

obtaining physical examination information and information of a plurality of distribution objects, the physical examination information comprising abnormal physical examination information and workload information of the physical examination information, and the information of the plurality of distribution objects comprising specialty information and workload information of the plurality of distribution objects;

inputting the physical examination information and the information of the plurality of distribution objects into an information matching model obtained by pre-training to obtain a matching degree between the physical examination information and the plurality of distribution objects, wherein the information matching model is configured to calculate the matching degree between the physical examination information and the plurality of distribution objects according to the abnormal physical examination information, the workload information of the physical examination information, and the specialty information and the workload information of the plurality of distribution objects; and determining a target distribution object from the plurality of distribution objects according to the matching degree between the physical examination information and each of the plurality of distribution objects, and distributing the physical examination information to the target distribution object;

wherein the information matching model comprises a semantic vector model and a vector matching model, and the operation of inputting the physical examination information and the information of the plurality of distribution objects into an information matching model obtained by pre-training to obtain a matching degree between the physical examination information and the plurality of distribution objects comprises:

inputting the physical examination information and the information of the plurality of distribution objects into the semantic vector model to output a first vector; and inputting the first vector into the vector matching model to output the matching degree between the physical examination information and the plurality of distribution objects;

wherein the operation of inputting the first vector into the vector matching model to output the matching degree between the physical examination information and the plurality of distribution objects comprises:

calculating, by the vector matching model, the matching degree between the physical examination information and the plurality of distribution objects based on a formula as below:

score = $W_2^T \sigma(W_1 V_{[cls]} + b_1)$, wherein the score represents the matching degree between the physical examination information and the plurality of distribution objects, the $V_{[cls]}$ represents the first vector, the $W_1$ represents a first mapping matrix of the vector matching model, and the $W_2^T$ represents a transposition of a second mapping matrix $W_2$ of the vector matching model, the b1 represents a bias matrix of the vector matching model, and the σ represents an activation function of the vector matching model.

14. The electronic device according to claim 13, wherein the operation of inputting the physical examination information and the information of the plurality of distribution objects into the semantic vector model to output a first vector comprises:
  splicing the physical examination information and the information of the plurality of distribution objects to obtain spliced information, wherein a header of the spliced information employs a marker symbol [CLS], and a separator [SEP] is employed between the physical examination information and the information of the plurality of distribution objects; and
  inputting the spliced information into the semantic vector model to output the first vector.

15. The electronic device according to claim 13, wherein operations further comprise:
  obtaining a plurality of training sample pairs, each of the plurality of training sample pairs being a first sample pair or a second sample pair, the first sample pair comprising sample physical examination information and information of a first sample distribution object, the second sample pair comprising the sample physical examination information and information of a second sample distribution object, wherein the matching degree of the first sample pair is greater than that of the second sample pair, the sample physical examination information comprises abnormal sample physical examination information, information of a sample distribution object comprises specialty information of the sample distribution object, and the sample distribution object is the first sample distribution object or the second sample distribution object;
  inputting the training sample pair into a model to be trained to obtain the matching degree of the training sample pair; and
  training the model to be trained according to the matching degree of the first sample pair, the matching degree of the second sample pair, workload information of the sample physical examination information, and workload information of each of the sample distribution objects, to determine the model to be trained after training as the information matching model.

16. The electronic device according to claim 15, wherein the operation of training the model to be trained according to the matching degree of the first sample pair, the matching degree of the second sample pair, workload information of the sample physical examination information, and workload information of each of the sample distribution objects, to determine the model to be trained after training as the information matching model comprises:
  training the model to be trained with a goal of ensuring a differential between the matching degree of the first sample pair and the matching degree of the second sample pair to be greater than a first preset threshold, and a first parameter of each of the sample distribution objects to be equal, wherein the first preset threshold is greater than zero, the first parameter is configured for characterizing the workload of each of the sample distribution objects, and the first parameter is determined by the workload information of the sample physical examination information.

* * * * *